(12) United States Patent
Raeppel et al.

(10) Patent No.: US 8,455,484 B2
(45) Date of Patent: *Jun. 4, 2013

(54) SELECTED INHIBITORS OF PROTEIN TYROSINE KINASE ACTIVITY

(75) Inventors: Stéphane Raeppel, St. Lazare (CA); Lijie Zhan, Montreal (CA); Stephen William Claridge, Montreal (CA); Franck Raeppel, Montreal (CA); Frédéric Gaudette, Sherbrooke (CA); Arkadii Vaisburg, Kirkland (CA)

(73) Assignee: MethylGene Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/082,944

(22) Filed: Apr. 8, 2011

(65) Prior Publication Data

US 2011/0257175 A1    Oct. 20, 2011

Related U.S. Application Data

(60) Provisional application No. 61/324,803, filed on Apr. 16, 2010.

(51) Int. Cl.
*A61K 31/5377* (2006.01)
*A61K 31/496* (2006.01)
*A61K 31/4365* (2006.01)
*C07D 413/14* (2006.01)
*C07D 471/04* (2006.01)

(52) U.S. Cl.
USPC ............ 514/233.8; 514/253.04; 514/301; 544/127; 544/362; 546/114

(58) Field of Classification Search
USPC ............ 514/233.8, 253.04, 301; 544/127, 544/362; 546/114
See application file for complete search history.

(56) References Cited

U.S. PATENT DOCUMENTS

2006/0074056 A1 * 4/2006 Vaisburg et al. ............ 514/151

\* cited by examiner

*Primary Examiner* — Samantha Shterengarts
(74) *Attorney, Agent, or Firm* — Wood, Phillips, Katz, Clark & Mortimer

(57) ABSTRACT

The invention provides new compounds and compositions thereof. The invention also provides methods for treating ophthalmic diseases, disorders and conditions.

15 Claims, No Drawings

SELECTED INHIBITORS OF PROTEIN TYROSINE KINASE ACTIVITY

RELATED APPLICATION

This application claims the benefit of U.S. Provisional Application Ser. No. 61/324,803, filed Apr. 16, 2010. The entire teachings of the above-referenced application are incorporated herein by reference.

BACKGROUND OF THE INVENTION

1. Field of the Invention

This invention relates to compounds that inhibit protein tyrosine kinase activity. In particular the invention relates to compounds that inhibit the protein tyrosine kinase activity of growth factor receptors, resulting in the inhibition of receptor signaling, for example, the inhibition of VEGF receptor signaling and HGF receptor signaling. More particularly, the invention relates to compounds, compositions and methods for the treatment of ophthalmic diseases, disorders or conditions.

2. Summary of the Related Art

Tyrosine kinases may be classified as growth factor receptor (e.g. EGFR, PDGFR, FGFR and erbB2) or non-receptor (e.g. c-src and bcr-abl) kinases. The receptor type tyrosine kinases make up about 20 different subfamilies. The non-receptor type tyrosine kinases make up numerous subfamilies. These tyrosine kinases have diverse biological activity. Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Aberrant or inappropriate protein kinase activity can contribute to the rise of disease states associated with such aberrant kinase activity.

For example, tyrosine kinases contribute to the pathology of ophthalmic diseases, disorders and conditions, such as age-related macular degeneration (AMD) and diabetic retinopathy (DR). Blindness from such diseases has been linked to anomalies in retinal neovascularization. Angiogenesis is an important component of certain normal physiological processes such as embryogenesis and wound healing, but aberrant angiogenesis contributes to some pathological disorders. The formation of new blood vessels is regulated by growth factors such as VEGF and HGF that activate receptor tyrosine kinases resulting in the initiation of signaling pathways leading to plasma leakage into the macula, causing vision loss. Kinases are thus attractive targets for the treatment of eye diseases involving neovascularization.

Thus, there is a need to develop a strategy for controlling neovascularization of the eye and to develop a strategy for the treatment of ophthalmic diseases.

Here we describe small molecules that are potent inhibitors of protein tyrosine kinase activity.

BRIEF SUMMARY OF THE INVENTION

The present invention provides new compounds and compositions thereof. The present invention also provides methods for treating an ophthalmic disease, disorder or condition with such compounds or compositions thereof. The compounds of the invention are inhibitors of kinase activity, such as protein tyrosine kinase activity, for example protein tyrosine kinase activity of growth factor receptors, or for example receptor type tyrosine kinase signaling.

In a first aspect, the invention provides compounds having the structure

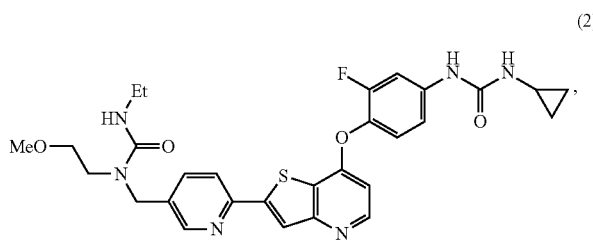

(2)

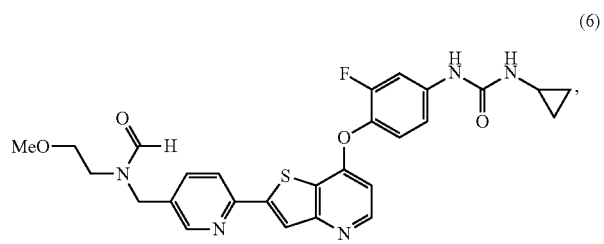

(6)

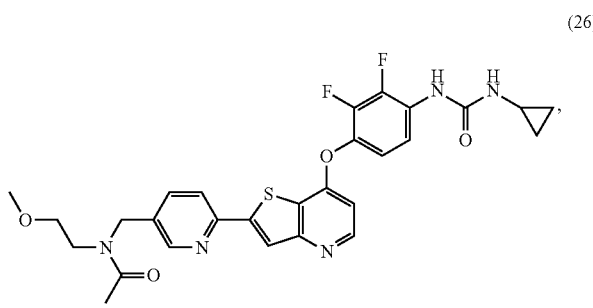

(26)

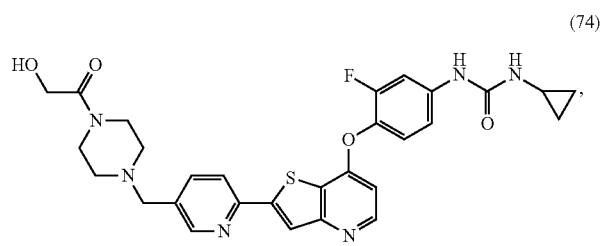

(74)

-continued

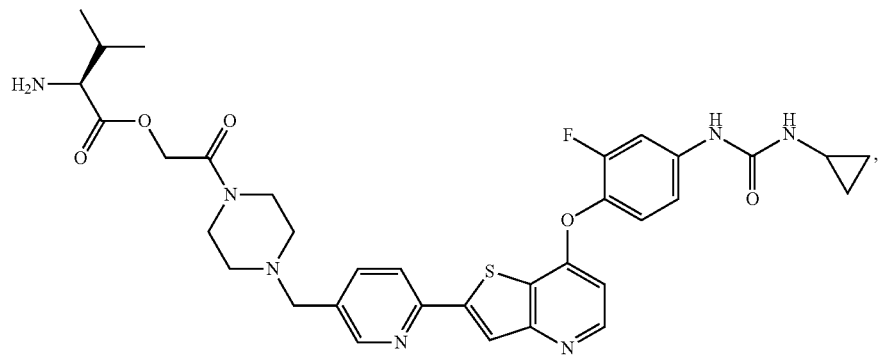 [SMILES: CC(C)[C@H](N)C(=O)OCC(=O)N1CCN(Cc2ccc(-c3cc4nccc(Oc5ccc(NC(=O)NC6CC6)cc5F)c4s3)nc2)CC1 ; "."]

(80)

(100)

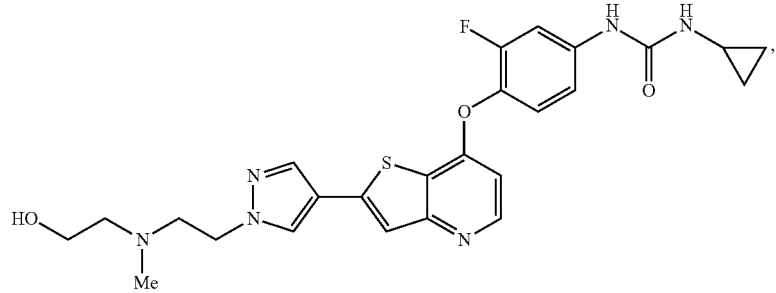 [SMILES: CN(CCO)CCn1cc(-c2cc3nccc(Oc4ccc(NC(=O)NC5CC5)cc4F)c3s2)cn1 ; "."]

(151)

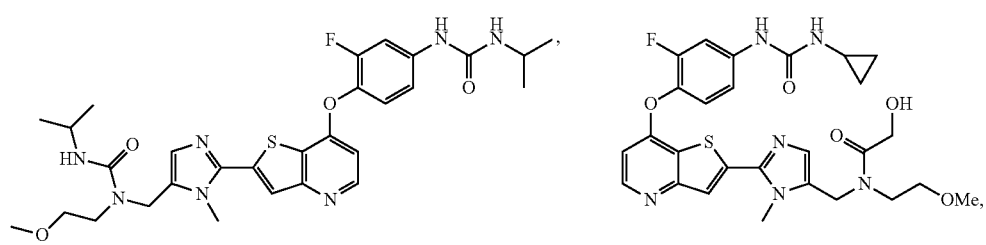

(192) (209)

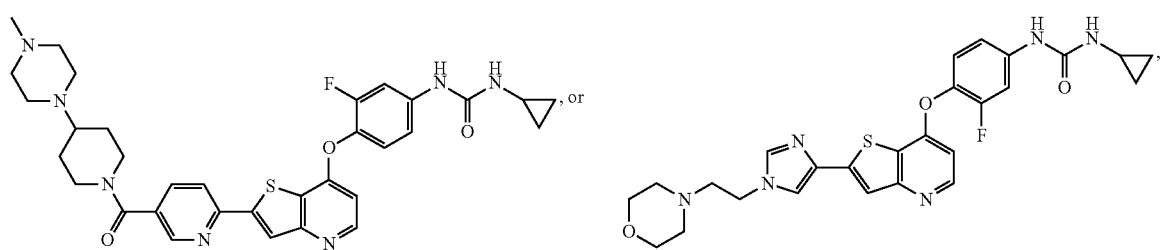

(234) (265)

and hydrates, solvates, pharmaceutically acceptable salts, prodrugs and complexes thereof, and racemic and scalemic mixtures, diastereomers and enantiomers thereof.

In a second aspect, the invention provides compositions comprising a compound according to the present invention and a pharmaceutically acceptable carrier, excipient or diluent.

In a third aspect, the invention provides a method of treating an ophthalmic disease, disorder or condition, the method comprising administering to a patient in need thereof a therapeutically effective amount of a compound according to the present invention, or a therapeutically effective amount of a composition according to the present invention. In some embodiments of this aspect, the disease is caused by choroidal angiogenesis. In some embodiments of this aspect, the disease is age-related macular degeneration, diabetic retinopathy or retinal edema. In some embodiments of this aspect, the patient is a mammal, for example a primate, for example a human.

In a fifth aspect, the invention provides for the use of a compound according to the present invention for or in the manufacture of a medicament to treat an ophthalmic disease, disorder or condition. In some embodiments of this aspect, the ophthalmic disease, disorder or condition is caused by choroidal angiogenesis. In some embodiments of this aspect, the disease is age-related macular degeneration, diabetic retinopathy or retinal edema.

In a sixth aspect, the invention provides for the use of a compound according to the present invention, or a composition thereof, to treat an ophthalmic disease, disorder or condition. In some embodiments of this aspect, the ophthalmic disease, disorder or condition is caused by choroidal angiogenesis. In some embodiments of this aspect, the disease is age-related macular degeneration, diabetic retinopathy or retinal edema.

The foregoing merely summarizes some aspects of the invention and is not intended to be limiting in nature. These aspects and other aspects and embodiments are described more fully below.

DETAILED DESCRIPTION

The invention provides new compounds, and compositions thereof. The present invention also provides methods for treating an ophthalmic disease, disorder or condition with such compounds or compositions thereof. The patent and scientific literature referred to herein reflects knowledge that is available to those with skill in the art. The issued patents, published patent applications, and references that are cited herein are hereby incorporated by reference to the same extent as if each was specifically and individually indicated to be incorporated by reference. In the case of inconsistencies, the present disclosure will prevail.

The terms "kinase inhibitor" and "inhibitor of kinase activity", and the like, are used to identify a compound which is capable of interacting with a kinase and inhibiting its enzymatic activity.

The term "inhibiting kinase enzymatic activity", and the like, is used to mean reducing the ability of a kinase to transfer a phosphate group from a donor molecule, such as ATP, to a specific target molecule (substrate). For example, the inhibition of kinase activity may be at least about 10%. In some embodiments of the invention, such reduction of kinase activity is at least about 25%, alternatively at least about 50%, alternatively at least about 75%, and alternatively at least about 90%. In other embodiments, kinase activity is reduced by at least 95% and alternatively by at least 99%. The $IC_{50}$ value is the concentration of kinase inhibitor which reduces the activity of a kinase to 50% of the uninhibited enzyme.

The terms "inhibitor of VEGF receptor signaling" is used to identify a compound having a structure as defined herein, which is capable of interacting with a VEGF receptor and inhibiting the activity of the VEGF receptor. In some embodiments, such reduction of activity is at least about 50%, alternatively at least about 75%, and alternatively at least about 90%. In some embodiments, activity is reduced by at least 95% and alternatively by at least 99%.

The term "inhibiting effective amount" is meant to denote a dosage sufficient to cause inhibition of kinase activity. The amount of a compound of the invention which constitutes an "inhibiting effective amount" will vary depending on the compound, the kinase, and the like. The inhibiting effective amount can be determined routinely by one of ordinary skill in the art. The kinase may be in a cell, which in turn may be in a multicellular organism. The multicellular organism may be, for example, an animal, for example a mammal and for example a human.

In an exemplary embodiment, such inhibition is specific, i.e., the kinase inhibitor reduces the ability of a kinase to transfer a phosphate group from a donor molecule, such as ATP, to a specific target molecule (substrate) at a concentration that is lower than the concentration of the inhibitor that is required to produce another, unrelated biological effect. For example, the concentration of the inhibitor required for kinase inhibitory activity is at least 2-fold lower, alternatively at least 5-fold lower, alternatively at least 10-fold lower, and alternatively at least 20-fold lower than the concentration required to produce an unrelated biological effect.

Thus, the invention provides a method for inhibiting kinase enzymatic activity, comprising contacting the kinase with an inhibiting effective amount of a compound or composition according to the invention. In some embodiments, the kinase is in an organism. Thus, the invention provides a method for inhibiting kinase enzymatic activity in an organism, comprising administering to the organism an inhibiting effective amount of a compound or composition according to the invention. In some embodiments, the organism is a mammal, for example a domesticated mammal. In some embodiments, the organism is a human.

The term "therapeutically effective amount" as employed herein is an amount of a compound of the invention, that when administered to a patient, elicits the desired therapeutic effect. The therapeutic effect is dependent upon the disease being treated and the results desired. As such, the therapeutic effect can be treatment of a disease-state. Further, the therapeutic effect can be inhibition of kinase activity. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art.

In some embodiments, the therapeutic effect is treatment of an ophthalmic diseases, disorder or condition. The phrase "treatment of an ophthalmic disease, disorder or condition" is intended to mean the ability of a compound according to the present invention to treat (a) a disease disorder or condition caused by choroidal angiogenesis, including, without limitation, age-related macular degeneration, or (b) diabetic retinopathy or retinal edema. In some embodiments the phrase "treatment of an ophthalmic disease, disorder or condition" is intended to mean the ability of a compound according to the present invention to treat an exudative and/or inflammatory ophthalmic disease, disorder or condition, a disorder related to impaired retinal vessel permeability and/or integrity, a disorder related to retinal microvessel rupture leading to focal hemorrhage, a disease of the back of the eye, a retinal disease, or a disease of the front of the eye, or other ophthalmic disease, disorder or condition.

In some embodiments, the ophthalmic disease, disorder or condition includes but is not limited to Age Related Macular Degeneration (ARMD), exudative macular degeneration (also known as "wet" or neovascular age-related macular degeneration (wet-AMD), macular oedema, aged disciform macular degeneration, cystoid macular oedema, palpebral oedema, retinal oedema, diabetic retinopathy, Acute Macular Neuroretinopathy, Central Serous Chorioretinopathy, chorioretinopathy, Choroidal Neovascularization, neovascular maculopathy, neovascular glaucoma, obstructive arterial and venous retinopathies (e.g. Retinal Venous Occlusion or Retinal Arterial Occlusion), Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angitis, Sickle Cell Retinopathy and other Hemoglobinopathies, Angioid Streaks, macular oedema occurring as a result of aetiologies such as disease (e.g. Diabetic Macular Oedema), eye injury or eye surgery, retinal ischemia or degeneration produced for example by injury, trauma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, an ocular inflammatory disease caused by bacterial or viral infection or by an ophthalmic operation, an ocular inflammatory disease caused by a physical injury to the eye, and a symptom caused by an ocular inflammatory disease including itching, flare, oedema and ulcer, erythema, erythema exsudativum multiforme, erythema nodosum, erythema annulare, scleroedema, dermatitis, angioneurotic oedema, laryngeal oedema, glottic oedema, subglottic laryngitis, bronchitis, rhinitis, pharyngitis, sinusitis, laryngitis or otitis media.

In some embodiments, the ophthalmic disease, disorder or condition is (a) a disease disorder or condition caused by choroidal angiogenesis, including, without limitation, age-related macular degeneration, or (b) diabetic retinopathy or retinal edema.

In some embodiments, the ophthalmic disease, disorder or condition includes but is not limited to age-related macular degeneration, diabetic retinopathy, retinal edema, retinal vein occlusion, neovascular glaucoma, retinopathy of prematurity, pigmentary retinal degeneration, uveitis, corneal neovascularization or proliferative vitreoretinopathy.

In some embodiments, the ophthalmic disease, disorder or condition is age-related macular degeneration, diabetic retinopathy or retinal edema.

Thus, the invention provides a method for treating an ophthalmic disease, disorder or condition in an animal, comprising administering to an animal in need of such treatment a therapeutically effective amount of a compound or composition of the invention. In some embodiments, the animal is a mammal, for example a domesticated mammal. In some embodiments, the animal is a human.

In some embodiments, the therapeutic effect is inhibition of retinal neovascularization. The phrase "inhibition of retinal neovascularization" is intended to mean the ability of a compound according to the present invention to retard the growth of blood vessels in the eye, for example new blood vessels originating from retinal veins, for example, to retard the growth of new blood vessels originating from retinal veins and extending along the inner (vitreal) surface of the retina.

In an exemplary embodiment, retinal neovascularization is retarded by at least 25% as compared to retinal neovascularization of non-contacted blood vessels, alternatively at least 50%, alternatively at least 75%, alternatively at least 90%, alternatively at least 95%, and alternatively, at least 99%. Alternatively, retinal neovascularization is inhibited by 100% (i.e., the blood vessels do not increase in size or number). In some embodiments, the phrase "inhibition of retinal neovascularization" includes regression in the number or size of blood vessels, as compared to non-contacted blood vessels. Thus, a compound according to the invention that inhibits retinal neovascularization may induce blood vessel growth retardation, blood vessel growth arrest, or induce regression of blood vessel growth.

Thus, the invention provides a method for inhibiting retinal neovascularization in an animal, comprising administering to an animal in need of such treatment a therapeutically effective amount of a compound or composition of the invention. In some embodiments, the animal is a mammal, for example a domesticated mammal. In some embodiments, the animal is a human.

The term "patient" as employed herein for the purposes of the present invention includes humans and other animals, for example mammals. Thus the compounds, compositions and methods of the present invention are applicable to both human therapy and veterinary applications. In some embodiments the patient is a mammal, for example a human.

The terms "treating", "treatment", or the like, as used herein cover the treatment of a disease-state in an organism, and includes at least one of: (i) preventing the disease-state from occurring, in particular, when such animal is predisposed to the disease-state but has not yet been diagnosed as having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, such as eliminating or curing of the disease. In some embodiments of the present invention the organism is an animal, for example a mammal, for example a primate, for example a human. As is known in the art, adjustments for systemic versus localized delivery, age, body weight, general health, sex, diet, time of administration, drug interaction, the severity of the condition, etc., may be necessary, and will be ascertainable with routine experimentation by one of ordinary skill in the art. In some embodiments, the terms "treating", "treatment", or the like, as used herein cover the treatment of a disease-state in an organism and includes at least one of (ii), (iii) and (iv) above.

Examples of routes of administration include but are not limited to, systemic, periocular, retrobulbar, intracanalicular, intravitral injection, topical (for example, eye drops), subconjunctival injection, subtenon, transcleral, intracameral, subretinal, electroporation, and sustained-release implant. Other routes of administration, other injection sites or other forms of administration for ophthalmic situations will be known or contemplated by one skilled in the art and are intended to be within the scope of the present invention.

In some embodiments of the present invention, routes of administration include topical, subconjunctval injection, intravitreal injection, or other ocular routes, systemically, or other methods known to one skilled in the art to a patient following ocular surgery.

In some other embodiments of the present invention, routes of administration include topical, intravitreal, transcleral, periocular, conjunctival, subtenon, intracameral, subretinal, subconjunctival, retrobulbar, or intracanalicular.

In some embodiments of the present invention, routes of administration include topical administration (for example, eye drops), systemic administration (for example, oral or intravenous), subconjunctival injection, periocular injection, intravitreal injection, and surgical implant for local delivery.

In some embodiments of the present invention, routes of administration include intravitreal injection, periocular injection, and sustained-release implant for local delivery.

In some embodiments of the present invention, an intraocular injection may be into the vitreous (intravitreal), under the conjunctiva (subconjunctival), behind the eye (retrobulbar), into the sclera, under the Capsule of Tenon (sub-Tenon), or may be in a depot form.

In some embodiments of the present invention, administration is local, including without limitation, topical, intravitreal, periorbital, intraocular, and other local administration to the eye, the ocular and/or periocular tissues and spaces, including without limitation, via a delivery device.

The compounds of the present invention form salts which are also within the scope of this invention.

The term "salt(s)", as employed herein, denotes acidic salts formed with inorganic and/or organic acids. Pharmaceutically acceptable (i.e., non-toxic (exhibiting minimal or no undesired toxicological effects), physiologically acceptable) salts are preferred, although other salts are also useful, e.g., in isolation or purification steps which may be employed during preparation. Salts of the compounds of the invention may be formed, for example, by reacting a compound of the present invention with an amount of acid, such as an equivalent amount, in a medium such as one in which the salts precipitates or in an aqueous medium followed by lyophilization.

The compounds of the present invention which contain a basic moiety, an amine or a pyridine, pyrazole or imidazole ring, may form salts with a variety of organic and inorganic acids. Examples of acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemi sulfates, heptanoates, hexanoates, hydrochlorides, hydrobromides, hydroiodides, hydroxyethanesulfanotes (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

As used herein, the term "pharmaceutically acceptable salts" is intended to mean salts that retain the desired biological activity of the above-identified compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalene-disulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

In some embodiments of the invention, salts of the compounds of the present invention, may be formed with chiral or racemic acids or their diastereomers. The chiral centers of such acids may have the S or R configuration. The racemic forms can be resolved by physical methods, such as, for example, fractional crystallization, separation or crystallization of diastereomeric derivates or separation by chiral column chromatography. The individual optical isomers can be obtained either starting from chiral precursors/intermediates or from the racemates by any suitable method, including without limitation, conventional methods, such as, for example, salt formation with an optically active acid followed by crystallization. The invention also comprises all tautomeric forms of the compounds disclosed herein.

Another aspect of the invention provides compositions comprising a compound according to the present invention. For example, in some embodiments of the invention, a composition comprises a compound, or an N-oxide, hydrate, solvate, pharmaceutically acceptable salt, complex or prodrug of a compound according to the present invention present in at least about 30% enantiomeric or diastereomeric excess. In some embodiments of the invention, the compound, N-oxide, hydrate, solvate, pharmaceutically acceptable salt, complex or prodrug is present in at least about 50%, at least about 80%, or even at least about 90% enantiomeric or diastereomeric excess. In some embodiments of the invention, the compound, N-oxide, hydrate, solvate, pharmaceutically acceptable salt, complex or prodrug is present in at least about 95%, alternatively at least about 98% and alternatively at least about 99% enantiomeric or diastereomeric excess. In other embodiments of the invention, a compound, N-oxide, hydrate, solvate, pharmaceutically acceptable salt, complex or prodrug is present as a substantially racemic mixture.

The present invention also includes prodrugs of compounds of the invention. The term "prodrug" is intended to represent a compound covalently bonded to a carrier, which prodrug is capable of releasing the active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the present invention), amides (e.g., trifluoroacetylamino, acetylamino, and the like), and the like.

The compounds of the invention may be administered, for example, as is or as a prodrug, for example in the form of an in vivo hydrolyzable ester or in vivo hydrolyzable amide. An in vivo hydrolyzable ester of a compound of the invention containing a carboxy or hydroxy group is, for example, a pharmaceutically acceptable ester which is hydrolyzed in the human or animal body to produce the parent acid or alcohol. Suitable pharmaceutically acceptable esters for carboxy include $C_1$-$C_6$alkoxymethyl esters (e.g., methoxymethyl), $C_1$-$C_6$alkanoyloxymethyl esters (e.g., for example pivaloyloxymethyl), phthalidyl esters, $C_3$-$C_8$cycloalkoxycarbonyloxy-$C_1$-$C_6$alkyl esters (e.g., 1-cyclohexylcarbonyloxyethyl); 1,3-dioxolen-2-onylmethyl esters (e.g., 5-methyl-1,3-dioxolen-2-onylmethyl; and $C_1$-$C_6$alkoxycarbonyloxyethyl esters (e.g., 1-methoxycarbonyloxyethyl) and may be formed at any appropriate carboxy group in the compounds of this invention.

An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_1$-$C_6$alkyl or N,N-di-$C_1$-$C_6$alkyl amide such as N-methyl, N-ethyl, N-propyl, N,N-dimethyl, N-ethyl-N-methyl or N,N-diethyl amide.

Upon administration to a subject, the prodrug undergoes chemical conversion by metabolic or chemical processes to yield a compound of the present invention.

The present invention is also directed to solvates and hydrates of the compounds of the present invention. The term "solvate" refers to a molecular complex of a compound with one or more solvent molecules in a stoichiometric or non-stoichiometric amount. A molecular complex of a compound or moiety of a compound and a solvent can be stabilized by non-covalent intra-molecular forces such as, for example, electrostatic forces, van der Waals forces, or hydrogen bonds. Those skilled in the art of organic chemistry will appreciate that many organic compounds can form such complexes with solvents in which they are obtained, prepared or synthesized, or from which they are precipitated or crystallized. The term "hydrate" refers to a complex in which the one or more solvent molecules are water and includes monohydrates, hemi-hydrates, dihydrates, hexahydrates, and the like. The meaning of the words "solvate" and "hydrate" are well known to those skilled in the art. Techniques for the preparation of solvates are well established in the art (see, for example, Brittain, Polymorphism in Pharmaceutical solids. Marcel Dekker, New York, 1999; Hilfiker, Polymorphism in the Pharmaceutical Industry, Wiley, Weinheim, Germany, 2006).

In some embodiments of this aspect, the solvent is an inorganic solvent (for example, water). In some embodiments of this aspect, the solvent is an organic solvent (such as, but not limited to, alcohols, such as, without limitation, methanol, ethanol, isopropanol, and the like, acetic acid, ketones, esters, and the like). In certain embodiments, the solvent is one commonly used in the pharmaceutical art, is known to be innocuous to a recipient to which such solvate is administered (for example, water, ethanol, and the like) and in preferred embodiments, does not interfere with the biological activity of the solute.

Compounds

The invention is directed to compounds having the structure

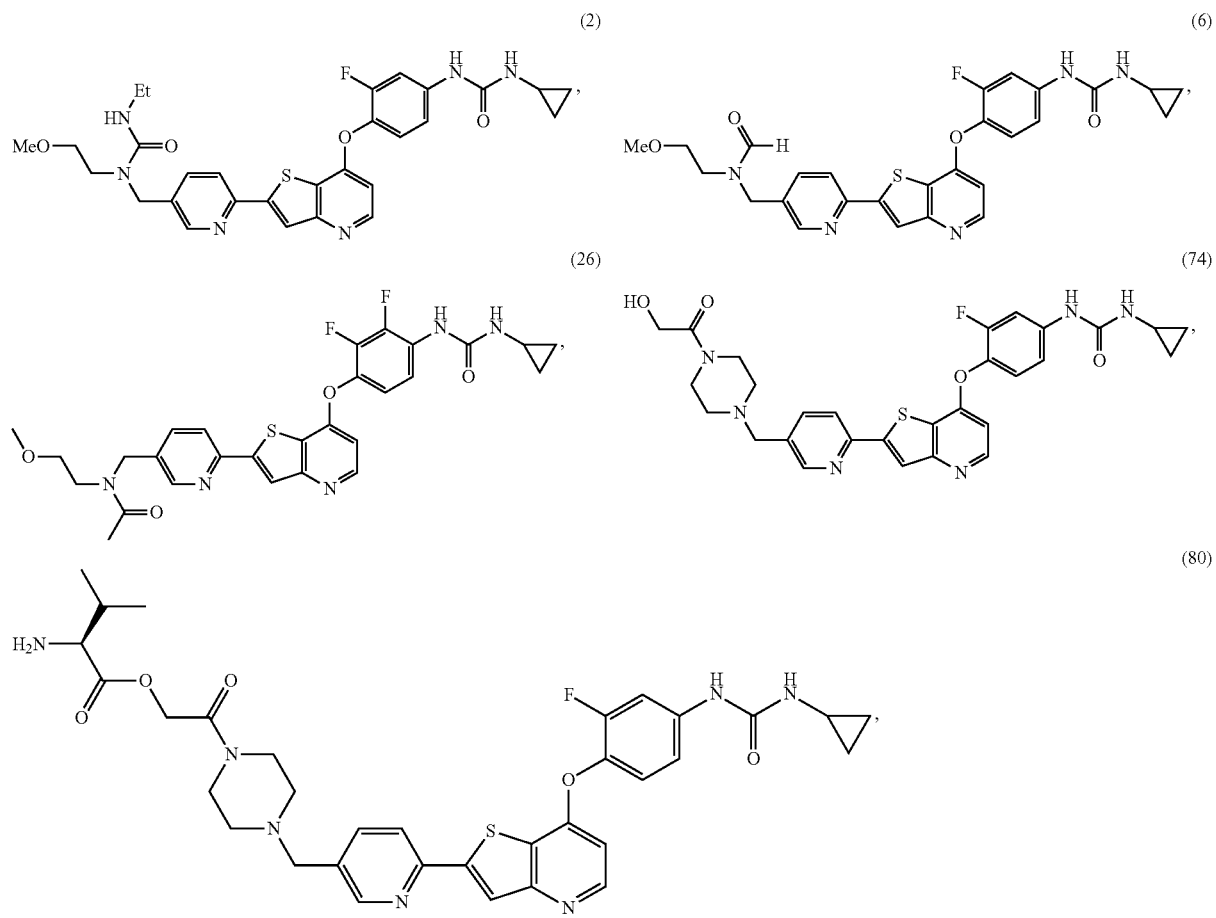

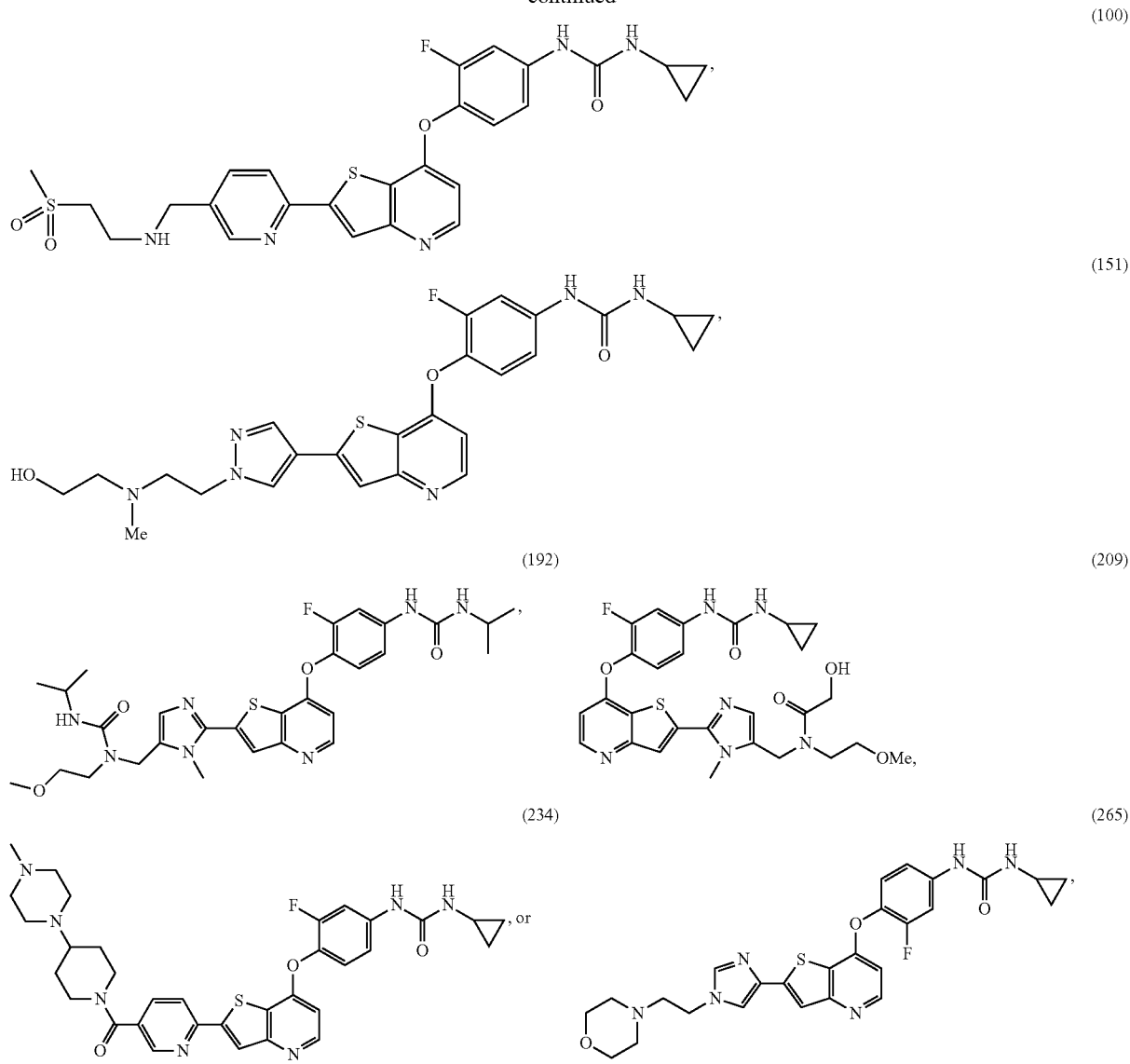

and hydrates, solvates, pharmaceutically acceptable salts, prodrugs and complexes thereof, and racemic and scalemic mixtures, diastereomers and enantiomers thereof.

The compounds of the present invention may generally be prepared according to the following Schemes. Tautomers and solvates (e.g., hydrates) of the compounds of above formulas are also within the scope of the present invention. Methods of solvation are generally known in the art. Accordingly, the compounds of the present invention may be in the free, hydrate or salt form, and may be obtained by methods exemplified by the following schemes below.

The following examples and preparations describe the manner and process of making and using the invention and are illustrative rather than limiting. It should be understood that there may be other embodiments which fall within the spirit and scope of the invention as defined by the claims appended hereto.

Compounds were named using Chemdraw Ultra (versions 10.0, 10.0.4 or version 8.0.3), which are available through Cambridgesoft (www.Cambridgesoft.com, 100 Cambridge Park Drive, Cambridge, Mass. 02140, or were derived therefrom.

The data presented herein demonstrate the inhibitory effects of the kinase inhibitors of the invention. These data lead one to reasonably expect that the compounds of the invention are useful not only for inhibition of kinase activity, protein tyrosine kinase activity, or embodiments thereof, such as, VEGF receptor signaling, but also as therapeutic agents for the treatment of ophthalmic diseases, disorders and conditions.

Synthetic Schemes and Experimental Procedures

The compounds of the invention can be prepared according to the reaction schemes or the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

All reagents and solvents were obtained from commercial sources and used as received. ¹H-NMR spectra were recorded on Mercury Plus Varian 400 MHz instrument in the solvents indicated. Low resolution mass-spectra (LRMS) were acquired on Agilent MSD instrument. Analytical HPLC was performed on Agilent 1100 instrument using Zorbax 3 μm, XDB-C8, 2.1×50 mm column; eluting with methanol/water containing 0.1% formic acid, with a gradient 5-95% methanol in 15 minutes. Automated column chromatography was performed on Biotage SP1 or Biotage SP4 instruments using Biotage® SNAP, SiliaSep™ or SiliaFlash® cartridges. Flash column chromatography was performed using silica gel (SiliaFlash F60, 40-63 μM, pore size 60 Å, SiliCycle®). Preparative column chromatography was performed on Gilson 215 instrument using Phenomenex Luna 15 μm, C18(2) 100 A, 250×21 mm column eluting with a mixture methanol/water containing 0.05% of formic acid, with a gradient 0-95% methanol in up to 60 minutes.

PARTICULAR EXAMPLES

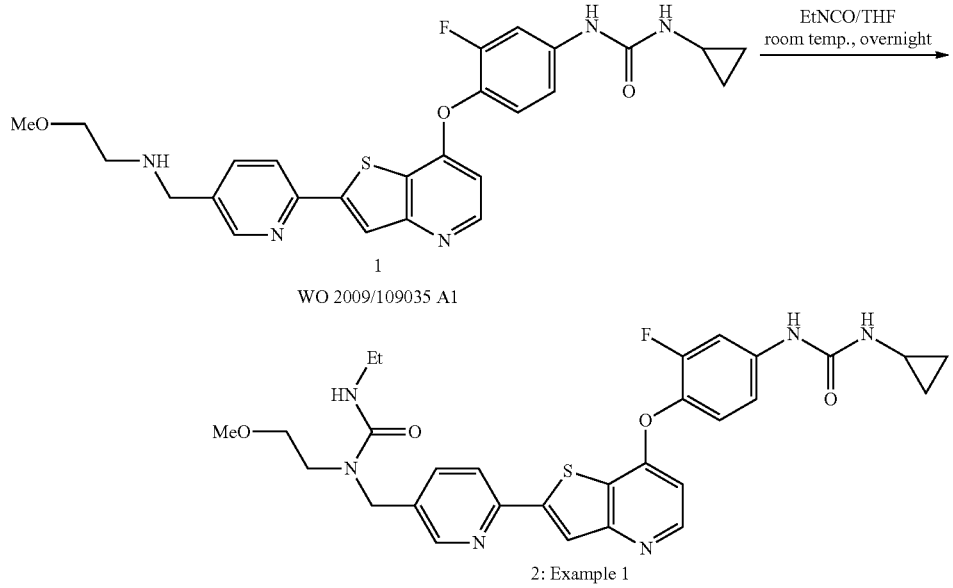

Example 1

N-[3-((6-(7-(4-(3-cyclopropylureido)-2-fluorophenoxy)thieno[3,2-b]pyridin-2-yl)pyridin-3-yl)methyl)]-N-(1-ethyl)-N-[3-(2-methoxyethyl)]urea (2)

A solution of 1-cyclopropyl-3-(3-fluoro-4-(2-(5-((2-methoxyethylamino)methyl)-pyridin-2-yl)thieno[3,2-b]pyridin-7-yloxy)phenyl)urea (1, 100 mg, 0.197 mmol,) and ethyl isocyanate (25 μL, 0.315 mmol) in THF (5 mL) was stirred (sonication for a while) at RT overnight. The reaction mixture was concentrated and purified by Biotage (SNAP 25 g cartridge; MeOH/DCM: 0/100 to 10/90 over 20 CV, then 10/90 over 5 CV). The desired fractions were collected and concentrated. The residue was co-precipitated in AcOEt (with traces of MeOH)/hexanes, collected by filtration, rinsed with hexanes, air-dried and dried under high vacuum to afford the title compound 2 (63 mg, 0.11 mmol, 56% yield) as a white fluffy solid. ¹H NMR (400 MHz, DMSO-$d_6$) δ (ppm): 8.73 (s, 1H), 8.52 (d, J=5.5 Hz, 1H), 8.48 (d, J=1.6 Hz, 1H), 8.31 (s, 1H), 8.24 (d, J=8.2 Hz, 1H), 7.78-7.69 (m, 2H), 7.38 (t, J=9.0 Hz, 1H), 7.24-7.17 (m, 1H), 6.64 (bd, J=5.4 Hz, 1H), 6.62-6.56 (m, 1H), 6.44 (t, J=5.4 Hz, 1H), 4.53 (s, 2H), 3.44-3.34 (m, 4H), 3.23 (s, 3H), 3.12-3.03 (m, 2H), 2.59-2.52 (m, 1H), 1.02 (t, J=7.1 Hz, 3H), 0.72-0.58 (m, 2H), 0.50-0.36 (m, 2H). MS (m/z): 579.46 (M+H).

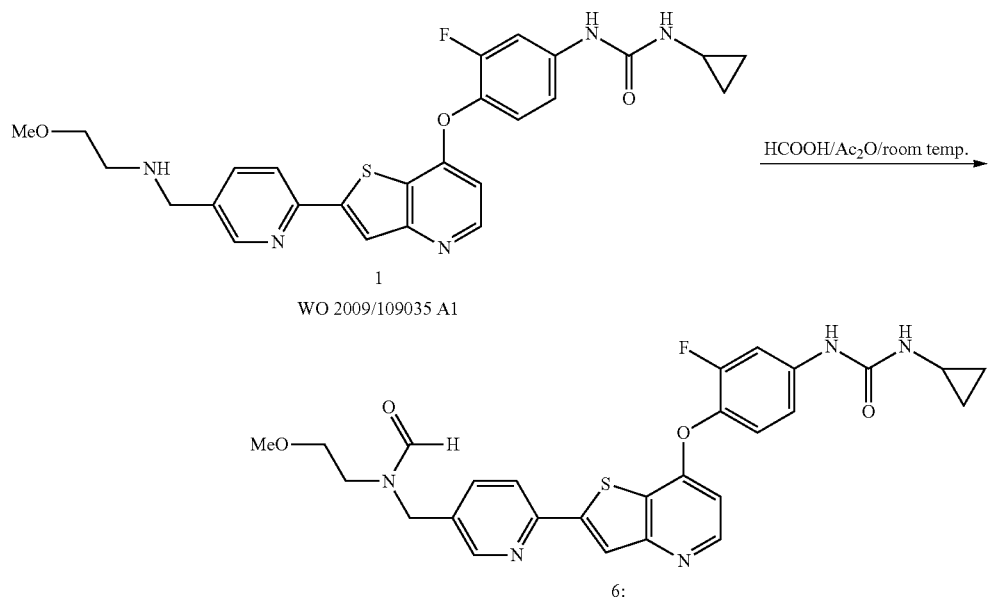

Example 2

N-((6-(7-(4-(3-cyclopropylureido)-2-fluorophenoxy) thieno[3,2-b]pyridin-2-yl)pyridin-3-yl)methyl)-N-(2-methoxyethyl)formamide (6)

To solution of acetic anhydride (150 μL, 1.17 mmol) in formic acid (2 mL) stirred at RT for 20 min was added in one portion 1 (150 mg, 0.296 mmol). After 2 hr, 200 μL of acetic anhydride (1.57 mmol) were added dropwise. The reaction mixture was stirred at RT overnight, quenched by addition of MeOH and concentrated. The residue was purified by Biotage (SNAP 25 g cartridge; MeOH/DCM: 0/100 to 10/90 over 20 CV, then 10/90 over 5 CV), to afford the title compound 6 (96 mg, 0.18 mmol, 76% yield) as an off-white fluffy solid. $^1$H NMR (400 MHz, DMSO-$d_6$) δ (ppm): mixture of rotamers, 8.75 (s, 1H), 8.60-8.50 (m, 2H), 8.37 and 8.34 (2s, 1H), 8.32-8.23 (m, 114), 8.15 (s, 1H), 7.90-7.77 (m, 1H), 7.73 (dd, J=13.5, 2.5 Hz, 1H), 7.38 (t, J=9.0 Hz, 1H), 7.20 (bd, J=10.2 Hz, 1H), 6.67-6.58 (m, 2H), 4.60 and 4.56 (2s, 2H), 3.46-3.36 (m, 4H), 3.21 and 3.19 (2s, 3H), 2.59-2.51 (m, 1H), 0.70-0.60 (m, 2H), 0.47-0.38 (m, 2H). MS (m/z): 536.4 (M+H).

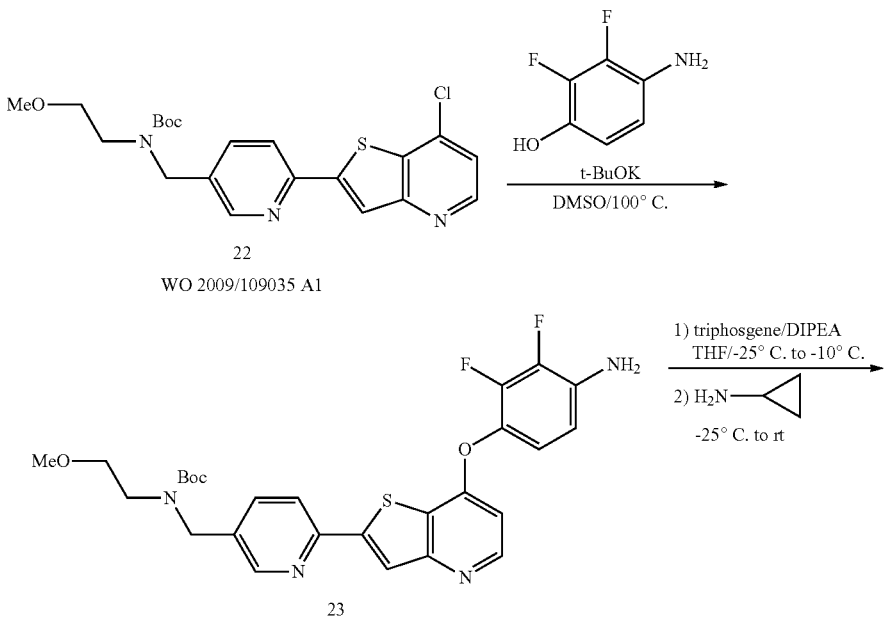

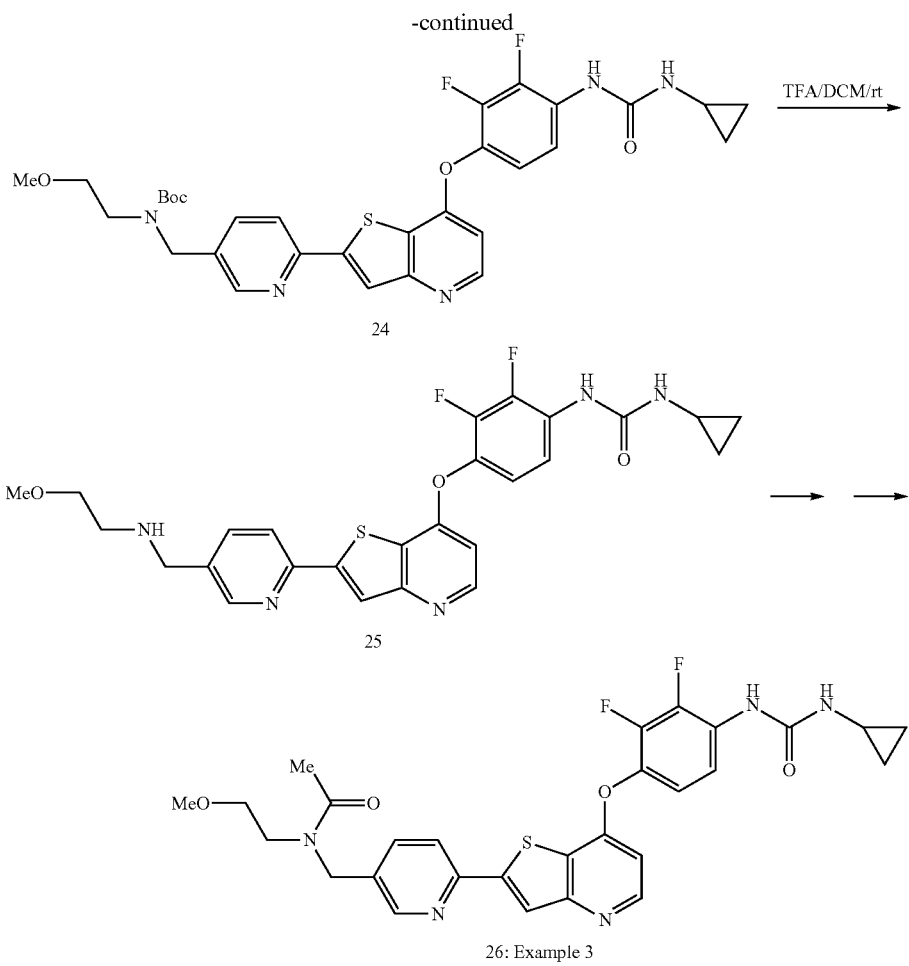

26: Example 3

Example 3

N-((6-(7-(4-(3-cyclopropylureido)-2,3-difluorophenoxy)thieno[3,2-b]pyridin-2-yl)-pyridin-3-yl)methyl)-N-(2-methoxyethyl)acetamide (26)

Step 1. tert-butyl (6-(7-(4-amino-2,3-difluorophenoxy)thieno[3,2-b]pyridin-2-yl)pyridin-3-yl)methyl(2-methoxyethyl)carbamate (23)

To a stirred solution of 4-amino-2,3-difluorophenol (1.471 g, 10.14 mmol) in DMSO (11.5 mL) at RT under nitrogen was added potassium tert-butoxide (1.345 g, 11.98 mmol). After 30 min, tert-butyl (6-(7-chlorothieno[3,2-b]pyridin-2-yl)pyridin-3-yl)methyl(2-methoxyethyl)carbamate (22, 4.0 g, 9.22 mmol) was added and the reaction mixture was heated at 100° C. for 2.5 h, then cooled to RT. The reaction mixture was poured into water (90 mL) and stirred for 30 min. A saturated aqueous solution of sodium chloride was added and the mixture was stirred at RT for 3 days. The solid was collected by filtration, rinsed with water, air-dried and dried under high vacuum. The crude product was purified by Biotage (40+M cartridge; AcOEt/hexanes:50/50 over 3 CV, 50/50 to 100% AcOEt over 6 CV, then 100% AcOEt over 8 CV), to provide a material that upon trituration with diethyl ether afforded title compound 23 (1.94 g, 3.58 mmol, 38% yield) as an off-white solid. MS (m/z): 543.3 (M+H).

Step 2. tert-butyl (6-(7-(4-(3-cyclopropylureido)-2,3-difluorophenoxy)thieno[3,2-b]-pyridin-2-yl)pyridin-3-yl)methyl(2-methoxyethyl (24)

To a stirred solution of aniline 23 (500 mg, 0.92 mmol) and DIPEA (0.8 mL, 4.61 mmol) in THF (18 mL) at −25° C. under nitrogen was added dropwise a solution of triphosgene (273 mg, 0.920 mmol) in THF (2 mL). The reaction mixture was stirred at −25° C. and cyclopropylamine (0.32 mL, 4.61 mmol) was slowly added. The reaction mixture was allowed to warm to RT over 1.5 h and stirred at RT overnight. The reaction mixture was then partitioned between AcOEt and water. The organic layer was successively washed with a saturated aqueous solution of ammonium chloride, 1N NaOH and brine, dried over anhydrous magnesium sulfate, filtered and concentrated to afford the title compound 24 as an off-white solid. The crude material was used in the next step without any further purification. MS (m/z): 626.6 (M+H).

Step 3. 1-cyclopropyl-3-(2,3-difluoro-4-(2-(5-((2-methoxyethylamino)methyl)pyridin-2-yl)thieno[3,2-b]pyridin-7-yloxy)phenyl)urea (25)

A solution of intermediate 24 (0.92 mmol) and TFA (10 mL) in DCM (50 mL) was stirred at RT for 3 h. The reaction mixture was concentrated, diluted with a minimum of MeOH and water was added. The pH was adjusted to ca pH12 with 4N NaOH. The fine suspension was sonicated for 15 min, collected by filtration, rinsed with water and dried under high vacuum to afford the title compound 25 (578 mg, 0.9 mmol, 98% yield, TFA salt) as a pale ivory solid. $^1$H NMR (400

MHz, DMSO-d$_6$) δ (ppm): 8.78-8.61 (m, 1H), 8.57 (d, J=1.6 Hz, 1H), 8.53 (d, J=5.5 Hz, 1H), 8.33 (s, 1H), 8.23 (d, J=8.2 Hz, 1H), 8.02 (t, J=7.8 Hz, 1H), 7.90 (dd, J=8.1, 2.1 Hz, 1H), 7.28 (td, J=9.0, 2.1 Hz, 1H), 7.16-7.01 (m, 1H), 6.75 (d, J=5.3 Hz, 1H), 3.78 (d, J=6.1 Hz, 2H), 3.41 (t, J=5.7 Hz, 2H), 3.24 (s, 3H), 2.65 (q, J=6.0 Hz, 2H), 2.61-2.53 (m, 1H), 2.30-2.21 (m, 1H), 0.72-0.58 (m, 2H), 0.49-0.36 (m, 2H). MS (m/z): 526.6 (M+H).

Step 4. N-((6-(7-(4-(3-cyclopropylureido)-2,3-difluorophenoxy)thieno[3,2-b]pyridin-2-yl)-pyridin-3-yl)methyl)-N-(2-methoxyethyl)acetamide (26)

A suspension of compound 25 (100 mg, 0.156 mmol, TFA salt) in acetic anhydride (1 mL) was stirred at RT for 2 days. The reaction mixture was quenched by addition of methanol and water. The fine suspension was collected by filtration, rinsed successively with water, 1N NaOH, water, and air-dried. The crude product was purified by Biotage (SNAP 25 g cartridge; MeOH/DCM: 0/100 to 10/90 over 20 CV, then 10/90 over 5 CV) to afford the title compound 26 (34 mg, 0.06 mmol, 38% yield) as a white solid. $^1$H NMR (400 MHz, DMSO-d$_6$) δ (ppm): mixture of rotamers, 8.57-8.44 (m, 3H), 8.38 and 8.34 (2s, 1H), 8.30 and 8.24 (2d, J=8.2 Hz, 1H), 8.04 (bt, J=8.3 Hz, 1H), 7.82-7.75 (m, 1H), 7.32-7.25 (m, 1H), 6.87 (bd, J=2.7 Hz, 1H), 6.79-6.74 (m, 1H), 4.71 and 4.59 (2s, 2H), 3.54-3.40 (m, 4H), 3.24 and 3.21 (2s, 3H), 2.61-2.53 (m, 1H), 2.13 and 2.05 (2s, 3H), 0.73-0.58 (m, 2H), 0.50-0.36 (m, 2H). MS (m/z): 568.6 (M+H).

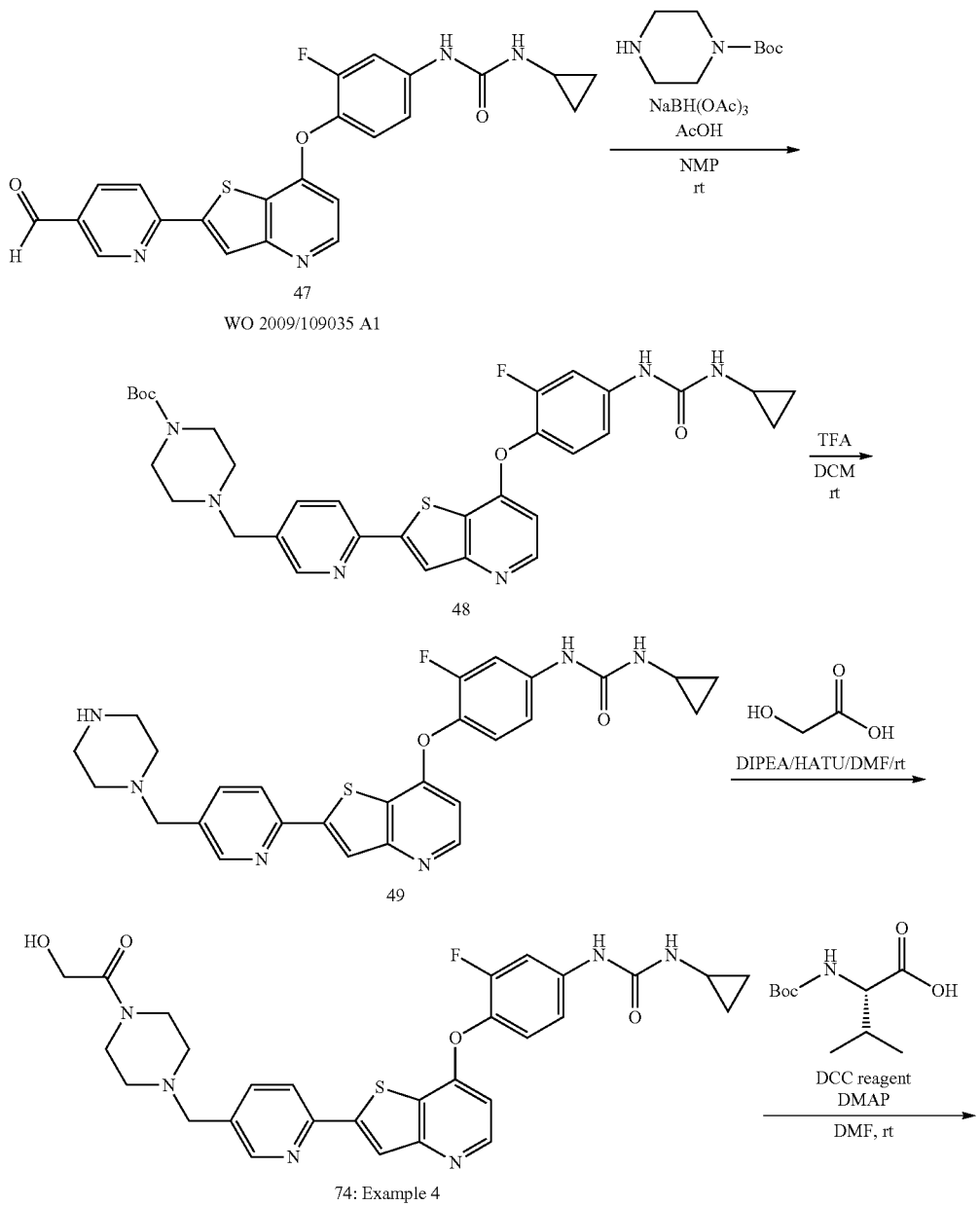

Scheme 4

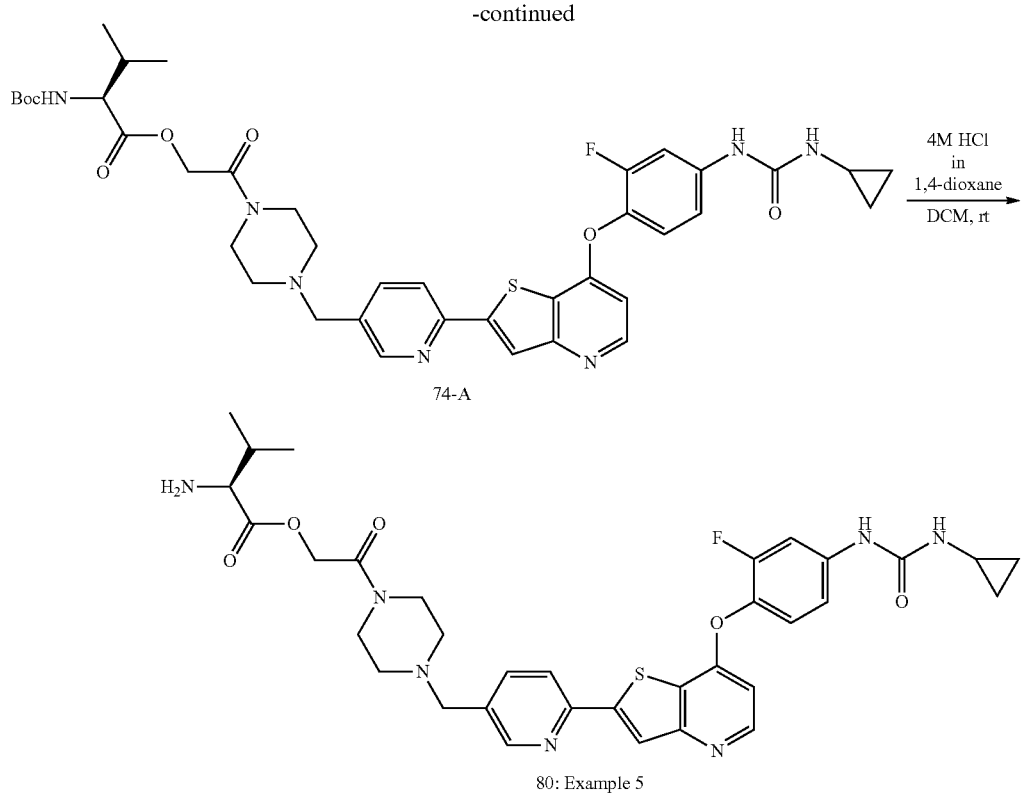

74-A

80: Example 5

Example 4

1-cyclopropyl-3-(3-fluoro-4-(2-(5-((4-(2-hydroxy-acetyl)piperazin-1-yl)methyl)pyridin-2-yl)thieno[3,2-b]pyridin-7-yloxy)phenyl)urea (74)

Step 1. tert-butyl 4-((6-(7-(4-(3-cyclopropylureido)-2-fluorophenoxy)thieno[3,2-b]-pyridin-2-yl)pyridin-3-yl)methyl)piperazine-1-carboxylate (48)

A suspension of 1-cyclopropyl-3-(3-fluoro-4-(2-(5-formylpyridin-2-yl)thieno[3,2-b]pyridin-7-yloxy)phenyl) urea (47, 3 g, 5.90 mmol, acetate salt), 1-boc-piperazine (1.65 g, 8.85 mmol) and acetic acid (675 μL, 11.80 mmol) in NMP (50 mL) at RT under nitrogen was sonicated for 3 h in order to obtain a solution, then NaBH(OAc)$_3$ (3.95 g, 17.70 mmol) was added. The reaction mixture was stirred at RT for 3 days then quenched by addition of water. The pH was adjusted to 12-13 with 4N NaOH and the suspension was stirred and sonicated for 1 h. The solid was collected by filtration, rinsed with water and air-dried. The residue was purified twice by Biotage (SNAP 50 g KP-Sil cartridge; MeOH/DCM: 1/99 to 10/90 over 20 CV). The desired fractions were collected, concentrated, and co-precipitated with AcOEt with traces of methanol/hexanes to afford the compound 48 (1.511 g, 2.44 mmol, 41% yield) as a white fluffy solid. $^1$H NMR (400 MHz, DMSO-d$_6$) δ (ppm): 8.71 (s, 1H), 8.56 (bd, J=2.0 Hz, 1H), 8.52 (d, J=5.5 Hz, 1H), 8.33 (s, 1H), 8.25 (d, J=8.2 Hz, 1H), 7.87 (dd, J=8.1, 2.1 Hz, 1H), 7.73 (dd, J=13.6, 2.4 Hz, 1H), 7.38 (t, J=9.1 Hz, 1H), 7.20 (bdd, J=8.8, 1.2 Hz, 1H), 6.65 (d, J=5.3 Hz, 1H), 6.57 (bd, J=2.5 Hz, 1H), 3.57 (s, 2H), 4H are hidden by water's peak, 2.59-2.51 (m, 1H), 2.42-2.27 (m, 4H), 1.39 (s, 9H), 0.72-0.58 (m, 2H), 0.50-0.36 (m, 2H). MS (m/z): 619.4 (M+H).

Step 2. 1-cyclopropyl-3-(3-fluoro-4-(2-(5-piperazin-1-ylmethyl)pyridin-2-yl)thieno[3,2-b]-pyridin-7-yloxy)phenyl)urea (49)

A solution of 48 (1.456 g, 2.35 mmol) and TFA (15 mL) in DCM (50 mL) was stirred at RT for 5 hr. The TFA was removed by co-evaporation with DCM, the residue was diluted with water, and the pH was adjusted to ~12-13 with 1N NaOH. The resultant suspension was sonicated for 15 min. The solid was collected by filtration, rinsed with water and dried under high vacuum to afford the compound 49 (1.227 g, traces of TFA) as an off-white fluffy solid. $^1$H NMR (400 MHz, DMSO-d$_6$) δ (ppm): 8.76 (bs, 1H), 8.54 (d, J=1.4 Hz, 1H), 8.52 (d, J=5.5 Hz, 1H), 8.32 (s, 1H), 8.24 (d, J=8.2 Hz, 1H), 7.85 (dd, J=8.1, 2.1 Hz, 1H), 7.73 (dd, J=13.5, 2.3 Hz, 1H), 7.38 (t, J=9.1 Hz, 1H), 7.20 (bd, J=10.2 Hz, 1H), 6.64 (d, J=5.5 Hz, 1H), 6.62 (bs, 1H), 3.58-3.48 (m, 2H), 2.73-2.64 (m, 4H), 2.59-2.52 (m, 1H), 2.38-2.25 (m, 4H), 0.69-0.62 (m, 2H), 0.46-0.40 (m, 2H), one NH is missing. MS (m/z): 519.6 (M+1I).

Step 3. 1-cyclopropyl-3-(3-fluoro-4-(2-(5-((4-(2-hydroxyacetyl)piperazin-1-yl)methyl)pyridin-2-yl)thieno[3,2-b]pyridin-7-yloxy)phenyl)urea (74)

To a stirred solution of compound 49 (122 mg, 0.235 mmol, scheme 15), glycolic acid (36 mg, 0.47 mmol) and DIPEA (123 μL, 0.71 mmol) in DMF (4 mL) under nitrogen was added HATU reagent (224 mg, 0.59 mmol), and the reaction mixture was stirred at RT overnight. The reaction mixture was then quenched by addition of water and 1N NaOH, stirred for 2 h, and extracted with DCM. The combined organic extract was dried over anhydrous magnesium sulfate, filtered and concentrated. The residue was purified twice by Biotage (SNAP 25 g cartridge; 2% of ammonium hydroxide in MeOH/DCM: 0/100 to 10/90 over 20 CV; then SiliaFlash 40 g cartridge, 2% of ammonium hydroxide in MeOH/DCM: 0/100 to 10/90 over 20 CV then 10/90 to 15/85 over 20CV) to produce a material that upon trituration with MeOH afforded the title compound 74 (53 mg, 0.09 mmol, 39% yield) as a white solid. $^1$H NMR (400 MHz. DMSO-$d_6$) δ (ppm): 8.77-8.69 (m, 1H), 8.57 (d, J=1.6 Hz, 1H), 8.52 (d, J=5.5 Hz, 1H), 8.34 (s, 1H), 8.26 (d, J=8.0 Hz, 1H), 7.88 (dd, J=8.1, 2.1 Hz, 1H), 7.73 (dd, J=13.5, 2.3 Hz, 1H), 7.38 (t, J=9.1 Hz, 1H), 7.20 (bd, J=9.2 Hz, 1H), 6.65 (d, J=4.9 Hz, 1H), 6.63-6.56 (m, 1H), 4.55 (t, J=5.5 Hz, 1H), 4.07 (d, J=5.5 Hz, 2H), 3.60 (s, 2H), 3.53-3.43 (m, 2H), 2H are hidden, 2.59-2.51 (m, 1H), 2.45-2.33 (m, 4H), 0.72-0.58 (m, 2H), 0.50-0.36 (m, 2H). MS (m/z): 577.5 (M+H).

Example 5

Step 1. (S)-2-(4-((6-(7-(4-(3-cyclopropylureido)-2-fluorophenoxy)thieno[3,2-b]pyridin-2-yl)pyridin-3-yl)methyl)piperazin-1-yl)-2-oxoethyl 2-(tert-butoxycarbonylamino)-3-methylbutanoate (74-A)

To a stirred solution of 74 (117 mg, 0.20 mmol), Boc-L-valine (132 mg, 0.61 mmol) and DMAP (25 mg, 0.20 mmol) in anhydrous DMF (4 ml) under nitrogen was added DCC reagent (251 mg, 1.22 mmol), and the reaction mixture was stirred at rt for 24 h. The reaction mixture was partitioned between AcOEt and a saturated aqueous solution of sodium bicarbonate. After separation, the organic layer was successively washed with a saturated aqueous solution of sodium bicarbonate, a saturated aqueous solution of ammonium chloride and brine, dried over anhydrous magnesium sulfate, filtered and concentrated. The residue was purified by Biotage (Snap 25 g cartridge; MeOH/DCM: 1/99 to 10/90 over 20 CV, then 10/90 over 5 CV), to afford the desired product 74-A (151 mg, 0.195 mmol, 96% yield) as a colorless-white sticky foam. MS (m/z): 776.7 (M+H).

Step 2. (S)-2-(4-((6-(7-(4-(3-cyclopropylureido)-2-fluorophenoxy)thieno[3,2-b]pyridin-2-yl)pyridin-3-yl)methyl)piperazin-1-yl)-2-oxoethyl 2-amino-3-methylbutanoate (80)

A suspension of the Boc-valine ester 74-A (151 mg, 0.195 mmol) and a solution of HCl (0.49 ml, 1.95 mmol, 4M in 1,4-dioxane) in anhydrous DCM (10 ml) was stirred at rt for 2.5 h. The reaction mixture was concentrated and diluted with a saturated aqueous solution of sodium bicarbonate. The aqueous solution was extracted with DCM containing traces of methanol. The combined organic layer was dried over anhydrous magnesium sulfate, filtered and concentrated. The residue was purified by Biotage (Silia Flash 12 g cartridge; 2% of ammonium hydroxide in MeOH/DCM: 1/99 to 15/85 over 20 CV, then 15/85 to 20/80 over 10 CV), to afford the desired product 80 (80 mg, 0.118 mmol, 60% yield) as an off-white sticky solid. $^1$H NMR (400 MHz, DMSO-$d_6$) δ (ppm): mixture of rotamers, 8.73 (s, 1H), 8.58 (bd, J=1.4 Hz, 1H), 8.52 (d, J=5.3 Hz, 1H), 8.34 (s, 1H), 8.26 (dd, J=8.1, 0.7 Hz, 1H), 7.88 (dd, J=8.2, 2.2 Hz, 1H), 7.73 (dd, J=13.6, 2.4 Hz, 1H), 7.38 (t, J=9.0 Hz, 1H), 7.20 (dd, J=9.0, 1.4 Hz, 1H), 6.65 (dd, J=5.3, 0.8 Hz, 1H), 6.59 (bd, J=2.5 Hz, 1H), 4.84 (d, J=14.7 Hz, 1H), 4.77 (d, J=14.9 Hz, 1H), 3.63-3.58 (m, 2H), 3.50-3.37 (m, 4H), 3.20 (d, J=5.1 Hz, 1H), 2.59-2.51 (m, 1H), 2.47-2.33 (m, 4H), 2.00-1.60 (m, 3H), 0.92 (d, J=6.8 Hz, 3H), 0.86 (d, J=6.8 Hz, 3H), 0.72-0.58 (m, 2H), 0.50-0.36 (m, 2H). MS (m/z): 577.6 and 676.7 (M+H).

Scheme 5

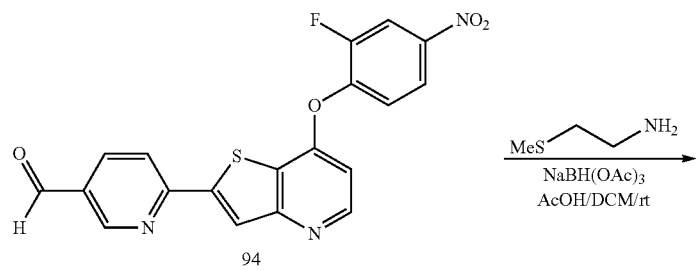

WO 2009/109035 A1

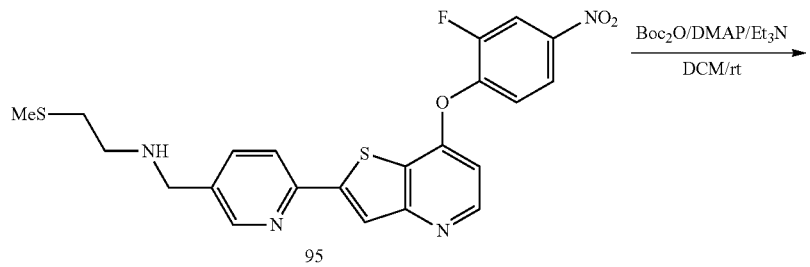

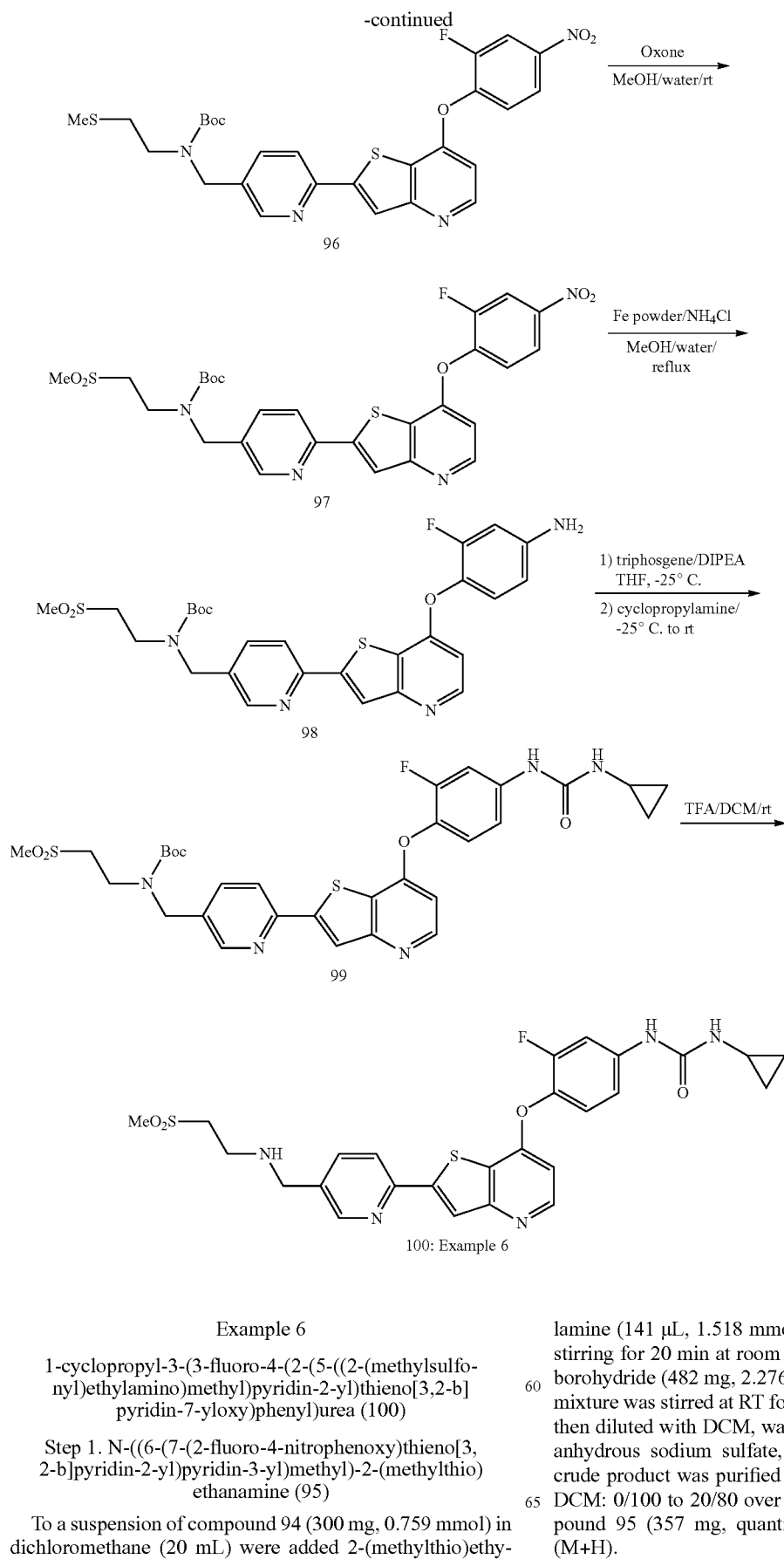

Example 6

1-cyclopropyl-3-(3-fluoro-4-(2-(5-((2-(methylsulfonyl)ethylamino)methyl)pyridin-2-yl)thieno[3,2-b]pyridin-7-yloxy)phenyl)urea (100)

Step 1. N-((6-(7-(2-fluoro-4-nitrophenoxy)thieno[3,2-b]pyridin-2-yl)pyridin-3-yl)methyl)-2-(methylthio)ethanamine (95)

To a suspension of compound 94 (300 mg, 0.759 mmol) in dichloromethane (20 mL) were added 2-(methylthio)ethylamine (141 µL, 1.518 mmol) and acetic acid (87 µl). After stirring for 20 min at room temperature, sodium triacetoxyborohydride (482 mg, 2.276 mmol) was added. The reaction mixture was stirred at RT for 16 h. The reaction mixture was then diluted with DCM, washed with 1N NaOH, dried over anhydrous sodium sulfate, filtered and concentrated. The crude product was purified by Biotage (Snap 50 g; MeOH/DCM: 0/100 to 20/80 over 20 CV), to afford the title compound 95 (357 mg, quantitative yield). MS (m/z): 471.5 (M+H).

Step 2. tert-butyl (6-(7-(2-fluoro-4-nitrophenoxy) thieno[3,2-b]pyridin-2-yl)pyridin-3-yl)methyl(2-(methylthio)ethyl)carbamate (96)

A mixture of 95 (357 mg, 0.759 mmol), Boc-anhydride (414 mg, 1.897 mmol), DMAP (93 mg, 0.759 mmol) and triethylamine (106 μL, 0.61 mmol) in DCM (20 mL) was stirred over weekend at RT. The reaction mixture was then concentrated, diluted with ethyl acetate, and successively washed with a saturated aqueous solution of sodium bicarbonate and a saturated aqueous solution of ammonium chloride, dried over anhydrous sodium sulfate, filtered and concentrated. The residue was purified by Biotage (SNAP 100 g cartridge; MeOH/DCM: 0/100 to 20/80 over 20 CV), to afford the title compound 96 (220 mg, 0.386 mmol, 50% yield). MS (m/z): 571.6 (M+H).

Step 3. tert-butyl (6-(7-(2-fluoro-4-nitrophenoxy) thieno[3,2-b]pyridin-2-yl)pyridin-3-yl)methyl(2-(methylsulfonyl)ethyl)carbamate (97)

To a solution of 96 (220 mg, 0.386 mmol) in MeOH (29 mL) and water (10 mL) was added Oxone™ (486 mg, 0.790 mmol). The reaction mixture was stirred overnight, concentrated, treated with 1N NaHSO₃ solution and the aqueous phase was extracted with ethyl acetate. The organic extract was washed with water, dried over anhydrous sodium sulfate, filtered and concentrated. The crude 97 (232 mg, 0.385 mmol) was used in the next step without any further purification. MS (m/z): 603.6 (M+H).

Step 4. tert-butyl (6-(7-(4-amino-2-fluorophenoxy) thieno[3,2-b]pyridin-2-yl)pyridin-3-yl)methyl (2-(methyl sulfonyl)ethyl)carbamate (98)

To a solution of 97 (232 mg, 0.385 mmol) in MeOH (17.5 mL) and water (1.75 mL) was added ammonium chloride (62 mg, 1.16 mmol) and iron powder (215 mg, 3.85 mmol). The reaction mixture was heated to reflux for 2 h, then at RT. The suspension was filtered through Celite™, rinsed with MeOH, and the filtrate was concentrated. The residue was purified by Biotage (SNAP 25 g cartridge; MeOH/DCM: 0/100 to 20/80 over 20 CV), to afford the title compound 98 (241 mg, quantitative yield). MS (m/z): 573.7 (M+H).

Step 5. tert-butyl (6-(7-(4-(3-cyclopropylureido)-2-fluorophenoxy)thieno[3,2-b]pyridin-2-yl)pyridin-3-yl)methyl(2-(methylsulfonyl)ethyl)carbamate (99)

To a solution of 98 (115 mg, 0.20 mmol) in THF (20 mL) at −25° C. was added DIPEA (140 μl, 0.80 mmol) followed by triphosgene (59.6 mg, 0.20 mmol). The reaction mixture was stirred at −25° C. for 1 h, then cyclopropylamine (71 μL, 1.00 mmol) was added and the reaction mixture was allowed to warm to RT. After stirring overnight, the reaction mixture was quenched by addition of methanol, concentrated, and partitioned between EtOAc and a saturated aqueous solution of ammonium chloride. The organic phase was dried over anhydrous sodium sulfate, filtered, and concentrated. The crude product was purified by Biotage (Snap 25 g; MeOH/DCM: 0/100 to 20/80 over 20 CV), to afford the title compound 99 (120 mg, 0.18 mmol, 91% yield). MS (m/z): 656.6 (M+H).

Step 6. 1-cyclopropyl-3-(3-fluoro-4-(2-(5-((2-(methylsulfonyl)ethylamino)methyl)-pyridin-2-yl)thieno[3,2-b]pyridin-7-yloxy)phenyl)urea (100)

To a solution of 99 (120 mg, 0.18 mmol) in DCM (20 mL) was added TFA (5.6 mL). The reaction mixture was stirred at RT overnight, concentrated, diluted with ethyl acetate, washed with a saturated aqueous solution of sodium bicarbonate, dried over anhydrous sodium sulfate, filtered and concentrated. The crude product was purified by Biotage (SNAP 25 g cartridge; MeOH/DCM: 0/100 to 20/80 over 20 CV), to afford the title compound 100 (90 mg, 0.13 mmol, 72% yield, TFA salt) as an off-white solid. ¹H NMR (400 MHz, DMSO-d₆) δ (ppm) δ 8.74 (s, 1H), 8.60 (s, 1H), 8.52 (d, J=5.2 Hz, 1H), 8.34 (s, 1H), 8.26 (d, J=8.4 Hz, 1H), 7.91 (d, J=8.0 Hz, 1H), 7.73 (dd, J=13.6, 2.4 Hz, 1H), 7.38 (t, J=8.8 Hz, 1H), 7.20 (d, J=10.0 Hz, 1H), 6.64 (d, J=5.2 Hz, 1H), 6.61 (s, 1H), 3.84 (s, 2H), 3.35-3.25 (m, 2H), 3.05 (s, 3H), 3.02-2.90 (m, 2H), 2.59-2.50 (m, 1H), 0.69-0.62 (m, 2H), 0.46-0.40 (m, 2H). MS (m/z): 556.5 (M+H).

Scheme 6

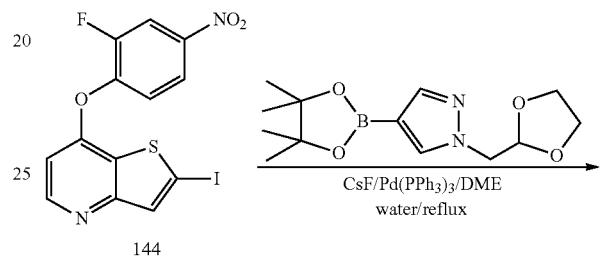

WO 2009/026717 A1

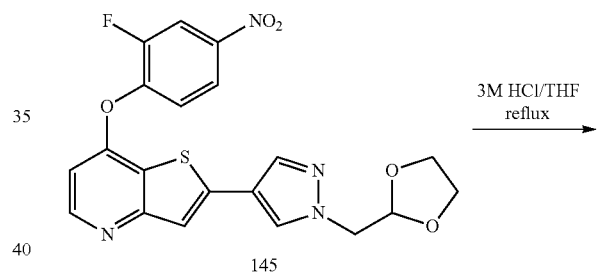

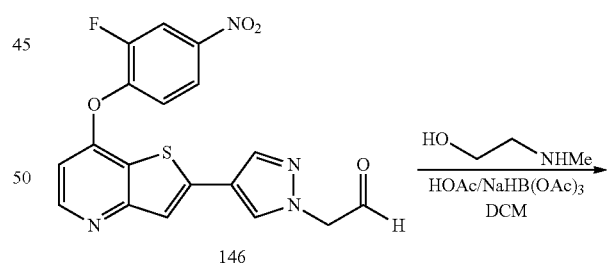

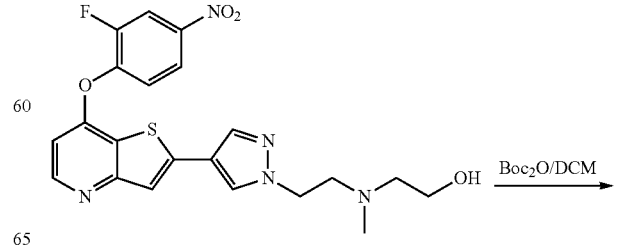

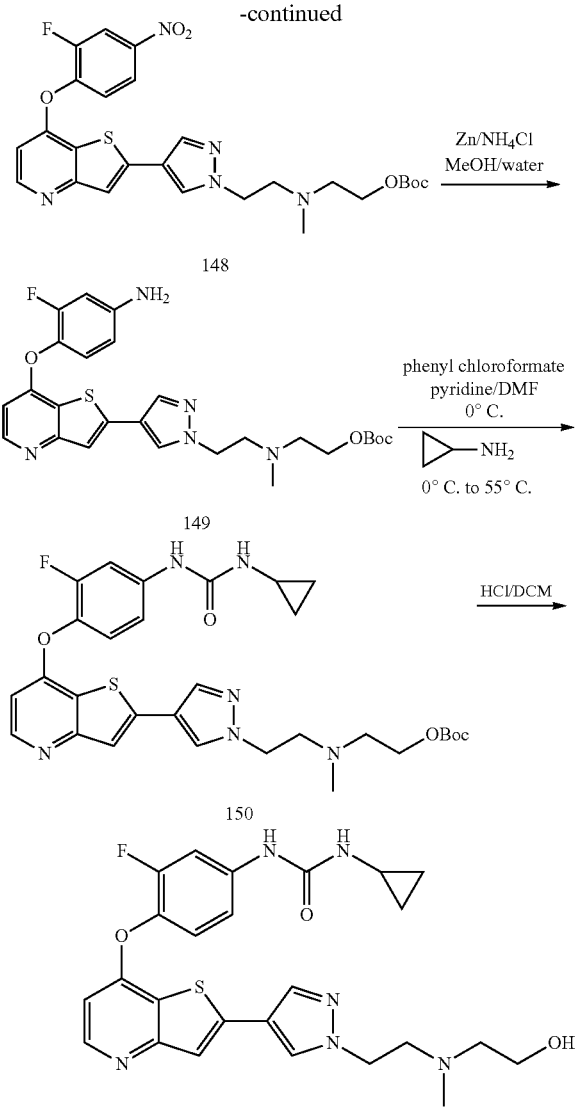

151: Example 7

Example 7

1-cyclopropyl-3-(3-fluoro-4-(2-(1-(2-((2-hydroxyethyl)(methyl)amino)ethyl)-1H-pyrazol-4-yl)thieno[3,2-b]pyridin-7-yloxy)phenyl)urea (151)

Step 1: 2-(1-((1,3-dioxolan-2-yl)methyl)-1H-pyrazol-4-yl)-7-(2-fluoro-4-nitrophenoxy)thieno[3,2-b]pyridine (145)

To a suspension 144 (3.57 g, 8.57 mmol) in DME (50 mL) and water (5 mL) was added 1-((1,3-dioxolan-2-yl)methyl)-4-(4,4,5,5-tetramethyl-1,3,2-dioxaborolan-2-yl)-1H-pyrazole (2 g, 7.14 mmol), CsF (3.25 g, 21.42 mmol), NaHCO$_3$ (1.799 g, 36 mmol) and Pd(PPh$_3$)$_4$ (0.825 g, 0.714 mmol), and the reaction mixture was heated to reflux overnight. The mixture was cooled to RT, diluted with EtOAc and washed with water. The organic phase was collected, dried over anhydrous Na$_2$SO$_4$, filtered and concentrated. The resultant solid was triturated with Et$_2$O to afford title compound 145 (3 g, 95% yield) as a beige solid. MS (m/z)=443.51 (M+H).

Step 2: 2-(4-(7-(2-fluoro-4-nitrophenoxy)thieno[3,2-b]pyridin-2-yl)-1H-pyrazol-1-yl)acetaldehyde (146)

To a solution of 145 (900 mg, 2.034 mmol) in THF (20 mL) was added 3M HCl (30 mL) and the reaction mixture was heated to reflux for 24 hours. The mixture was cooled to RT, and concentrated. The residual aqueous solution was treated with solid sodium bicarbonate and then extracted with DCM. The organic phase was collected, dried over anhydrous Na$_2$SO$_4$, filtered and concentrated. The crude aldehyde 146 (810 mg, 100% yield) was used in the next step with no additional purification. MS (m/z)=399.3 (M+H)

Step 3: 2-((2-(4-(7-(2-fluoro-4-nitrophenoxy)thieno[3,2-b]pyridin-2-yl)-1H-pyrazol-1-yl)ethyl)(methyl)amino)ethanol (147)

To a solution of 146 (810 mg, 2.033 mmol) in DCM (40 mL) was added HOAc (0.233 mL, 4.07 mmol) and 2-(methylamino)ethanol (305 mg, 4.07 mmol), and the reaction mixture was stirred at RT for an hour. Sodium triacetoxyborohydride (1.293 g, 6.10 mmol) was added and the mixture was stirred at RT overnight. The mixture was then diluted with saturated NaHCO$_3$ solution then solid NaHCO$_3$ was added to neutralize the acid. The DCM layer was collected, dried over anhydrous Na$_2$SO$_4$, filtered and concentrated to afford title compound 147 (930 mg, 100% yield) that was used directly in the next step with no additional purification. MS (m/z)=458.50 (M+H).

Step 4: tert-butyl 242-(4-(7-(2-fluoro-4-nitrophenoxy)thieno[3,2-b]pyridin-2-yl)-1H-pyrazol-1-yl)ethyl)(methyl)amino)ethyl carbonate (148)

To a solution of 147 (930 mg, 2.033 mmol) in DCM (40 mL) was added Boc$_2$O (1.331 g, 6.10 mmol) and DMAP (49.7 mg, 0.407 mmol) and the reaction mixture was stirred at RT overnight. The reaction mixture was concentrated and purified via column chromatography (eluent EtOAc to 20% MeOH in EtOAc) to afford title compound 148 (420 mg, 37% yield) as a brown oil. (MS (m/z)=558.49 (M+H)

Step 5: 242-(4-(7-(4-amino-2-fluorophenoxy)thieno[3,2-b]pyridin-2-yl)-1H-pyrazol-1-yl)ethyl)(methyl)amino)ethyl tert-butyl carbonate (149)

To a solution of 148 (420 mg, 0.753 mmol) in MeOH (20 mL) was added ammonium chloride (81 mg, 1.506 mmol) in water (5 mL) and zinc powder (197 mg, 3.01 mmol) and the reaction mixture was heated to reflux for 3 hours. The mixture was cooled to RT then filtered and the filtrate was concentrated under reduced pressure. The residue was dissolved in DCM and washed with water. The organic phase was collected, dried over anhydrous Na$_2$SO$_4$, filtered and concentrated to afford title compound 149 (397 mg, 100% yield) that was used directly in the next step with no additional purification. MS (m/z)=528.49 (M+H).

Step 6: tert-butyl 2-((2-(4-(7-(4-(3-cyclopropylureido)-2-fluorophenoxy)thieno[3,2-b]pyridin-2-yl)-1H-pyrazol-1-yl)methyl)(methyl)amino)ethyl carbonate (150)

To a stirred solution of 149 (0.397 mg, 0.752 mmol) and pyridine (0.183 mL, 2.257 mmol) in DMF (20 mL) at 0° C. under nitrogen was added phenyl chloroformate (295 mg, 1.881 mmol) and the reaction mixture was stirred at 0° C. for 2 hrs. Cyclopropylamine (215 mg, 3.76 mmol) was added and the reaction mixture was heated at 55° C. for 5 hrs. The reaction mixture was partitioned between EtOAc and saturated sodium bicarbonate solution, then washed a saturated ammonium chloride solution and brine, dried over anhydrous sodium sulfate, filtered and concentrated. The crude product was purified by column chromatography (EtOAc to 30% MeOH in EtOAc) to afford title compound 150 (150 mg, 33% yield) as a white solid. MS (m/z)=611.70 (M+H).

Step 7: 1-cyclopropyl-3-(3-fluoro-4-(2-(1-(2-((2-hydroxyethyl)(methyl)amino)ethyl)-1H-pyrazol-4-yl)thieno[3,2-b]pyridin-7-yloxy)phenyl)urea (151)

To a solution of 150 (150 mg, 0.246 mmol) in DCM (10 mL) was added HCl in dioxane (0.307 mL, 1.118 mmol) and the white precipitate was stirred at RT for 2 hrs. The mixture was diluted with saturated NaHCO$_3$ solution and stirred for 10 mins before the layers were separated. The organic phase was collected, dried over Na$_2$SO$_4$, filtered and concentrated. The residue was purified by column chromatography (eluent EtOAc to 30% MeOH in EtOAc) to afford title compound 151 (100 mg, 80% yield) as a white solid. $^1$H NMR (400 MHz, DMSO-d$_6$) δ (ppm): 8.43 (d, J=5.48 Hz, 1H), 7.84 (s, 1H), 7.77 (s, 1H), 7.63 (m, 1H), 7.47 (s, 7.17 (m, 2H), 7.03 (s, 1H), 6.45 (d, J=5.48 Hz, 1H), 4.92 (s, 1H), 4.27 (t, J=6.26 Hz, 2H), 3.56 (t, J=5.08 Hz, 2H), 2.95 (t, J=6.26 Hz, 2H), 2.60 (m, 3H), 2.34 (s, 3H), 0.91 (m, 2H), 0.72 (m, 2H). MS (m/z)=511.60 (M+H).

Scheme 7

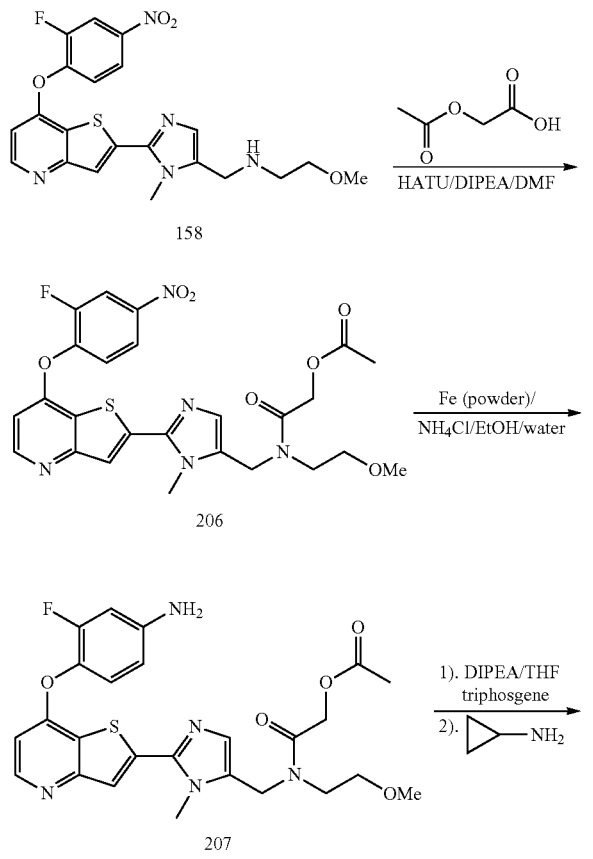

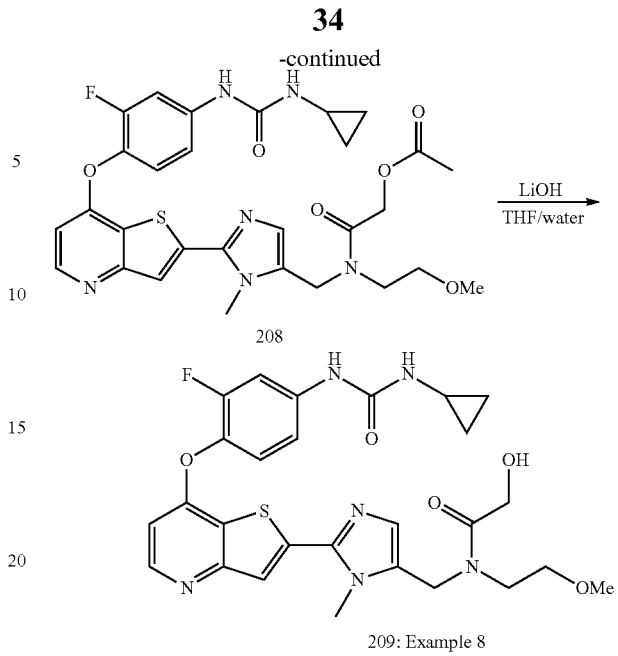

209: Example 8

Example 8

N-((2-(7-(4-(3-cyclopropylureido)-2-fluorophenoxy)thieno[3,2-b]pyridin-2-yl)-1-methyl-1H-imidazol-5-yl)methyl)-2-hydroxy-N-(2-methoxyethyl)acetamide (209)

Step 1: 2-(((2-(7-(2-fluoro-4-nitrophenoxy)thieno[3,2-b]pyridin-2-yl)-1-methyl-1H-imidazol-5-yl)methyl)(2-methoxyethyl)amino)-2-oxoethyl acetate (206)

To a solution of 158 (423 mg, 0.925 mmol) in DMF (18 mL) was added 2-acetoxyacetic acid (164 mg, 1.387 mmol), DIPEA (0.565 mL, 3.24 mmol) and HATU reagent (1055 mg, 2.77 mmol). The reaction mixture was stirred at room temperature for 1 hr followed by addition of NaHCO$_3$ saturated solution (200 mL) and EtOAc (300 mL). A white precipitate was formed which was collected by filtration and discarded. The organic layer of the filtrate was collected, dried over anhydrous sodium sulfate and concentrated to give a yellowish solid, which was triturated with ether to give title compound 206 (570 mg, 111% yield, crude) that was used in the next step with no additional purification. MS: 558 (MH)+.

Step 2: 2-(((2-(7-(4-amino-2-fluorophenoxy)thieno[3,2-b]pyridin-2-yl)-1-methyl-1H-imidazol-5-yl)methyl)(2-methoxyethyl)amino)-2-oxoethyl acetate (207)

The reaction mixture consisting of 206 (300 mg, 0.538 mmol), ammonium chloride (24.75 mg, 0.463 mmol) and iron powder (255 mg, 4.57 mmol) in ethanol (6 mL)/water (3.0 mL) was heated to reflux for 1 h. The reaction mixture was filtered while hot and concentrated. The residue was purified by Biotage (MeOH/DCM, 0-20%, SNAP 25 g cartridge) to give the title compound 207 (133 mg, 0.252 mmol, 47% yield) as a white solid. MS: 528 (MH)+.

Step 3: 2-(((2-(7-(4-(3-cyclopropylureido)-2-fluo-rophenoxy)thieno[3,2-b]pyridin-2-yl)-1-methyl-1H-imidazol-5-yl)methyl)(2-methoxyethyl)amino)-2-oxoethyl acetate (208)

To a solution of 207 (130 mg, 0.246 mmol) in THF (20 mL) at 0° C. was added DIPEA (0.172 mL, 0.986 mmol) and triphosgene (43.9 mg, 0.148 mmol). The reaction mixture was stirred for 1 hr at 0° C. before cyclopylamine (70.3 mg, 1.232 mmol) was added. The reaction mixture was allowed to warm up to room temperature and stirred for 1 hr before concentration. The residue was purified by Biotage (MeO/DCM, 0-20%, SNAP 25 g cartridge) to give the title compound 208 (104 mg, 0.170 mmol, 69% yield) as a white solid. MS: 611 (MH)+.

Step 4: N-((2-(7-(4-(3-cyclopropylureido)-2-fluo-rophenoxy)thieno[3,2-b]pyridin-2-yl)-1-methyl-1H-imidazol-5-yl)methyl)-2-hydroxy-N-(2-methoxy-ethyl)acetamide (209)

To a solution of 208 (104 mg, 0.170 mmol) in THF (18 mL) was added a solution of LiOH (32.6 mg, 1.362 mmol) in water (6 mL) and the mixture was stirred for 2 hr at room temperature before concentration. The residue was purified by Biotage (MeOH/DCM, 0-20%, SNAP 25 g cartridge) to give title compound 209 (40 mg, 0.070 mmol, 41% yield) as a white solid. $^1$H NMR (400 MHz, DMSO-d$_6$) δ (ppm): 8.75 (s, 1H), 8.55 (d, 1H, J=5.3 Hz), 7.94 (s, 1H), 7.75 (dd, 1H, J1=2.3 Hz, J2=13.5 Hz), 7.41 (t, 1H, J=9.0 Hz), 7.24-7.22 (m, 1H), 7.09 (s, 1H), 6.70 (d, 1H, J=5.5 Hz), 6.60 (m, 1H), 4.74 (s, 2H), 4.68-4.66 (m, 1H), 4.24 (d, J=5.7 Hz), 3.87 (s, 3H), 3.45 (m, 2H), 3.35 (s, 3H), 3.28 (m, 2H), 2.60-2.57 (m, 1H), 0.71-0.67 (m, 2H), 0.48-0.45 (m, 2H). MS: 569.6 (MH)+

192: Example 9

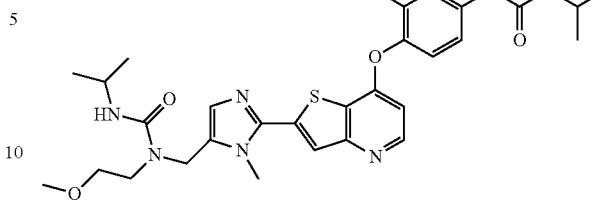

Example 9

1-((2-(7-(4-Isopropylaminocarbonylamino-2-fluo-rophenoxy)thieno[3,2-b]pyrid methyl-1H-imidazol-5-yl)methyl)-3-isopropyl-1-(2-methoxyethyl)urea (192)

Compound 192 was obtained by following the procedures similar to the ones used in the scheme 7 for the synthesis of compound 209 by replacing the 2-acetoxyacetic acid in the presence of DIPEA and HATU reagent with triphosgene followed by isopropylamine in the step 1, and cyclopropylamine with isopropylamine in the step 3. $^1$H NMR (400 MHz, DMSO-d$_6$) δ (ppm): 8.67 (s, 1H), 8.49 (d, J=5.5 Hz, 1H), 7.89 (s, 1H), 7.68 (dd, J1=2.6 Hz, J2=13.5 Hz, 1H), 7.34 (t, J=9.0 Hz, 1H), 7.12-7.09 (m, 1H), 6.94 (s, 1H), 6.64 (d, J=5.5 Hz, 1H), 6.14-6.09 (m, 2H), 4.55 (s, 2H), 3.83 (s, 3H), 3.80-3.74 (m, 2H), 3.38-3.27 (m, 4H), 3.21 (s, 3H), 2.06-1.04 (m, 12H). MS (m/z)=598.6 (M+H).

Scheme 8

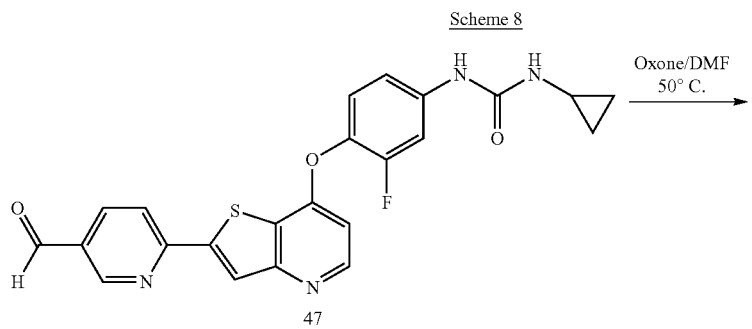

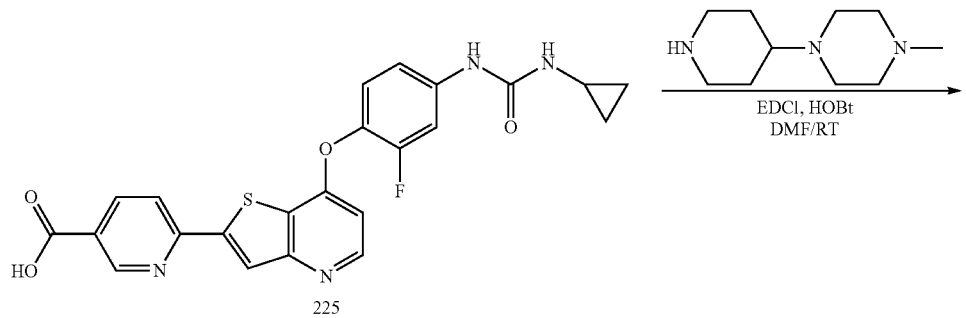

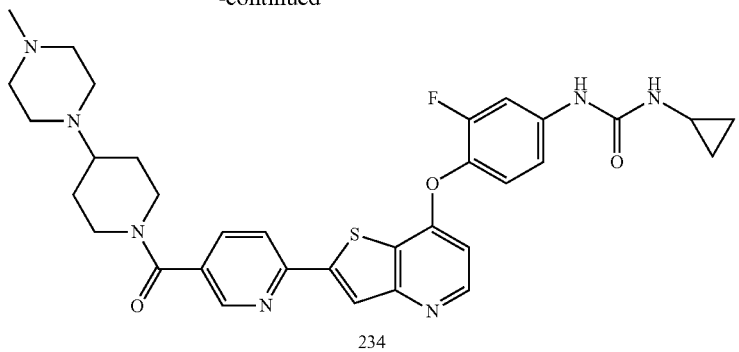

234

Example 10

1-Cyclopropyl-3-(3-fluoro-4-(2-(5-(4-(4-methylpiperazin-1-yl)piperidine-1-carbonyl)pyridin-2-yl)thieno[3,2-b]pyridin-7-yloxy)phenyl)urea (234)

Step 1: 6-(7-(4-(3-Cyclopropylureido)-2-fluorophenoxy)thieno[3,2-b]pyridin-2-yl)nicotinic acid (225)

To a suspension of aldehyde 47 (200 mg, 0.446 mmol) in DMF (10 mL) was added Oxone® (330 mg, 0.535 mmol) at RT and the reaction mixture was stirred at 50° C. for 16 hours. The reaction mixture was cooled to 0° C., treated with 1N aqueous HCl (20 mL) and stirred at RT for an additional hour. The resultant precipitate was collected by filtration, washed with water (30 mL) and dried. The crude product was triturated with MeOH to afford title compound 225 (165 mg, 80% yield) as a beige solid. NMR (400 MHz, CD$_3$OD) δ (ppm): 9.66 (bs, 1H), 8.98 (dd, J=1.9, 0.9 Hz, 1H), 8.51 (d, J=5.5 Hz, 1H), 8.31 (s, 1H), 8.22 (dd, J=8.1, 1.9 Hz, 1H), 8.17 (dd, J=8.1, 0.9 Hz, 1H), 7.77 (dd, J=13.7, 2.5 Hz, 1H), 7.45 (bs, 1H), 7.37 (t, J=9.1 Hz, 1H), 7.26 (dd, J=8.9, 1.5 Hz, 1H), 6.62 (d, J=5.3, 0.8 Hz, 1H), 2.60-2.52 (m, 1H), 0.69-0.56 (m, 2H), 0.50-0.37 (m, 2H). [Carboxylic OH is not seen]. MS: 465.3 (MH)$^+$

Step 2: 1-Cyclopropyl-3-(3-fluoro-4-(2-(5-(4-(4-methylpiperazin-1-yl)piperidine-1-carbonyl)pyridin-2-yl)thieno[3,2-b]pyridin-7-yloxy)phenyl)urea (234)

To a stirred solution of acid 225 (300 mg, 0.646 mmol) in DMF (10 mL) at 0° C. were added HOBT (198 mg, 1.292 mmol), EDC (248 mg, 1.292 mmol) and 1-methyl-4-(piperidin-4-yl)piperazine (118 mg, 0.646 mmol). The reaction mixture was stirred at room temperature overnight, diluted with NaHCO$_3$ saturated solution, and extracted with EtOAc. The extract was dried over anhydrous Na$_2$SO$_4$ and concentrated in vacuum. The residue was purified three times by Biotage (MeOH/EtOAc, 0-50%, 25 g column) followed by purification on Gilson [MeOH/H2O, 50-95%, HCOOH (0.05%)] to afford the title compound 234 (50 mg, 0.079 mmol, 12.29% yield) as a mono-formate salt. NMR (400 MHz, CD$_3$OD) δ (ppm): 8.67 (dd, J1=0.8 Hz, J2=2.1 Hz, 1H,), 8.48 (s, 1H), 8.47 (s, 1H), 8.19 (dd, J1=0.8 Hz, J2=8.3 Hz, 1H), 8.16 (s, 1H), 7.97 (dd, J1=2.2 Hz, J2=8.2 Hz, 1H), 7.65 (dd, J1=2.4 Hz, J2=13.1 Hz, 1H), 7.29 (t, 1H, J=8.8 Hz, 1H), 7.20-7.18 (m, 1H), 6.65 (dd, J1=0.8 Hz, J2=5.5 Hz, 1H), 3.83 (br. s, 1H), 3.24 (br s, 1H), 3.01 (br. s, 6H), 2.85 (br. s, 3H), 2.76-2.70 (m, 2H), 2.67 (s, 3H), 2.61-2.57 (m, 1H), 2.02 (br. s, 1H), 1.91-1.85 (br. s, 1H), 1.56-1.49 (hr. s, 2H), 0.78-0.74 (m, 2H), 0.55-0.51 (m, 2H). MS: 630.4 (MH)$^+$ Scheme 9

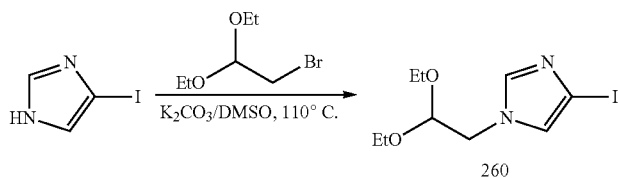

260

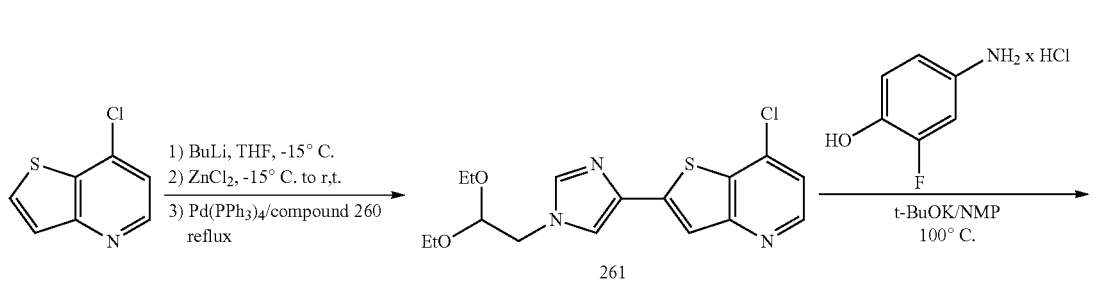

261

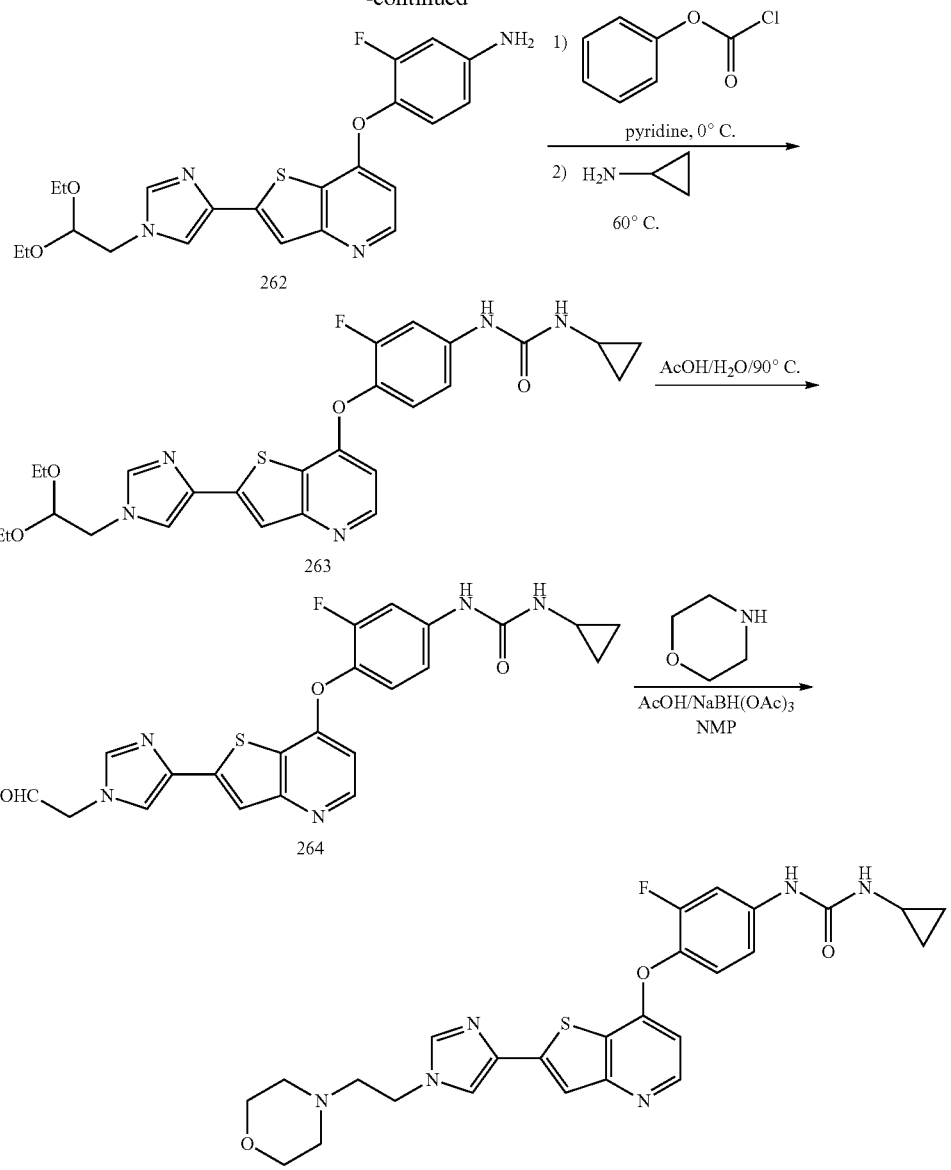

Example 11

1-cyclopropyl-3-(3-fluoro-4-(2-(1-(2-morpholinoethyl)-1H-imidazol-4-yl)thieno[3,2-b]pyridin-7-yloxyphenyl)urea (265)

Step 1. 1-(2,2-diethoxyethyl)-4-iodo-1H-imidazole (260) To a stirred solution of 4-iodoimidazole (10 g, 51.6 mmol) and bromoacetaldehyde diethyl acetal (9.31 mL) in DMSO (30 mL) was added $K_2CO_3$ (10.69 g, 77 mmol). The reaction mixture was heated at 110° C. for 16 h. After cooling to RT, the reaction mixture was diluted with water and extracted with AcOEt. The organic extract was washed with brine, dried over anhydrous sodium sulfate, filtered and concentrated. The residue was purified by Biotage (SNAP 80 g cartridge; AcOEt/Hex:0/100 to 50/50 over 20 CV). The desired fractions were collected and concentrated to afford title compound 260 (11.29 g, 36.4 mmol, 71% yield) as yellow oil. MS (m/z): 310.97 (M+H).

Step 2. 7-chloro-2-(1-(2,2-diethoxyethyl)-1H-imidazol-4-yl)thieno[3,2-b]pyridine (261)

To a stirred solution of 7-chlorothieno[3,2-b]pyridine (9.26 g, 54.6 mmol) in THF (88 mL) at −15° C. was added n-BuLi (21.84 mL, 54.6 mmol). After 30 min, a solution of $ZnCl_2$ 0.5M in THF (109 mL, 54.6 mmol) was added at −15° C. and the reaction mixture was warmed to RT over 45 min. A solution of palladium tetrakistriphenylphosphine (0.841 g, 0.73 mmol) and iodide 260 (11.29 g, 36.4 mmol) in THF (33 mL) was added and the mixture was heated to reflux for 3 h then concentrated. The residue was diluted with water and ammonium hydroxide and extracted with DCM. The organic extract was washed with brine, dried over anhydrous sodium sulfate, filtered and concentrated. The residue was purified by Biotage (SNAP 80 g cartridge; AcOEt/Hex:0/100 to 100/0 over 20 CV) to produce a material that upon trituration with MTBE afforded the title compound 261 (1.2 g, 3.41 mmol, 9% yield) as light-brown solid. MS (m/z): 437.45 (M+H).

Step 3. 4-(2-(1-(2,2-diethoxyethyl)-1H-imidazol-4-yl)thieno[3,2-b]pyridin-7-yloxy)-3-fluoroaniline (262)

To a stirred solution of 4-amino-2-fluorophenol hydrochloride (1.39 g, 8.53 mmol) in DMSO (20 mL) was added t-BuOK (1.99 g, 17.76 mmol). After 30 min, chloride 261 (2.5 g, 7.11 mmol) was added and the reaction mixture was heated at 100° C. for 1 h.

In a separate flask a solution of 4-amino-2-fluorophenol hydrochloride (1.39 g, 8.53 mmol) in DMSO (20 mL) was treated with t-BuOK (1.99 g, 17.76 mmol) and the resultant phenolate solution was added to the original reaction mixture at 100° C. After 30 min, the mixture was poured into water (300 mL) to form a precipitate that was collected by filtration and dried under high vacuum to afford the title compound 262 (2.86 g, 6.46 mmol, 91% yield) as light brown solid. MS (m/z): 443.44 (M+H).

Step 4. 1-cyclopropyl-3-(4-(2-(1-(2,2-diethoxyethyl)-1H-imidazol-4-yl)thieno[3,2-b]pyridine-7-yloxy)-3-fluorophenyl)urea (263)

To a stirred solution of amine 262 (2.86 g, 6.46 mmol) and pyridine (1.04 mL, 12.93 mmol) in DMF (50 mL) at 0° C. was added phenyl chloroformate (973 µl, 7.76 mmol). After 30 min, cyclopropylamine (1.14 mL, 16.16 mmol) was added at 0° C. and the reaction mixture was heated at 60° C. for 45 min. More cyclopropylamine (1 mL, 14.18 mmol) was added and the reaction mixture was heated at 60° C. for an additional 10 min. After cooling to RT, the reaction mixture was quenched by addition of water to form a precipitate. The solid was collected by filtration, washed with water and dried under vacuum for 2 h. The residue was purified by Biotage (SNAP 80 g cartridge; MeOH/DCM: 0/100 to 10/90 over 20 CV). The desired fractions were collected, concentrated, triturated with MTBE and dried under high vacuum to afford the title compound 263 (2.95 g, 5.61 mmol, 87% yield) as a pink solid. MS (m/z): 526.60 (M+H).

Step 5. 1-cyclopropyl-3-(3-fluoro-4-(2-(1-(2-oxoethyl)-1H-imidazol-4-yl)thieno[3,2-b]pyridin-7-yloxy)phenyl)urea (264)

To a solution of acetal 263 (2.95 g, 5.61 mmol) in AcOH/H$_2$O (20/20 mL) was added concentrated HCl (2 mL) and the reaction mixture was heated at 90° C. for 1 h. The reaction mixture was concentrated, diluted with water and 4M NaOH to pH 10 to form a precipitate that was collected by filtration, washed with water and dried under vacuum. The material was then purified by Biotage (SNAP 100 g cartridge; 2% of ammonium hydroxide in MeOH/DCM: 0/100 to 15/85, over 20 CV) to afford the title compound 264 (1.2 g, 2.66 mmol, 47% yield) as a brown solid. MS (m/z): 484.51 (M+H).

Step 6. 1-cyclopropyl-3-(3-fluoro-4-(2-O-(2-morpholinoethyl)-1H-imidazol-4-yl)thieno[3,2-b]pyridin-7-yloxy)phenyl)urea (265)

To a solution of 264 (200 mg, 0.443 mmol), morpholine (46 µl, 0.532 mmol) and AcOH (51 µl, 0.886 mmol) in NMP (10 mL) was added sodium triacetoxyborohydride (282 mg, 1.329 mmol) and the reaction mixture was stirred for 18 h at RT. The reaction mixture was quenched with water and extracted with DCM. The organic extract was successively washed with saturated ammonium chloride solution and brine, dried over anhydrous sodium sulfate, filtered and concentrated. The residue was purified by Biotage (SNAP 40 g cartridge; 2% of ammonium hydroxide in MeOH/DCM: 0/100 to 15/85 over 20 CV) and by Gilson (Phenomenex, Luna 15µ, C18(2) 100 A, 250×50.0 mm, 15 µm; 0.05% of formic acid in both MeOH/water:20/80 to 95/5 over 60 min, flow; 30 mL/min) to afford the title compound 265 (30 mg, 0.057 mmol, 13% yield, formate salt) as a white solid. $^1$H NMR (400 MHz, DMSO-d$_6$) δ (ppm): 9.52 (bs, 1H), 8.41 (d, J=5.6 Hz, 1H), 8.36 (bs, 1H), 7.92 (d, J=1.2 Hz, 1H), 7.78 (d, J=1.2 Hz, 1H), 7.71 (dd, J=2.4 and 14.0 Hz, 1H), 7.65 (s, 1H), 7.33 (t, J=9.2 Hz, 1H), 7.32 (bs, 1H), 7.22 (dd, J=1.6 and 8.8 Hz, 1H), 6.54 (d, J=5.6 Hz, 1H), 4.14 (t, J=6.0 Hz, 2H), 3.57 (t, J=4.4 Hz, 4H), 2.66 (t, J=6.4 Hz, 2H), 2.58-2.51 (m, 1H), 2.49-2.40 (m, 4H), 0.64-0.59 (m, 2H), 0.43-0.39 (m, 2H). MS (m/z): 523.55 (M+H).

Pharmaceutical Compositions

In some embodiments, the invention provides pharmaceutical compositions comprising a compound according to the invention and a pharmaceutically acceptable carrier, excipient, or diluent. Compositions of the invention may be formulated by any method well known in the art and may be prepared for administration by different routes, including, topical, intravitreal, periorbital, intraocular and other methods of local administration to the eye, the ocular and/or perioculary tissues and spaces, including via delivery devices. In some embodiments, administration may be by the oral route.

The characteristics of the carrier, excipient or diluent will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

The active compound is included in the pharmaceutically acceptable carrier, excipient or diluent in an amount sufficient to deliver to a patient a therapeutically effective amount without causing serious toxic effects in the patient treated. The effective dosage range of a pharmaceutically acceptable derivative can be calculated based on the weight of the parent compound to be delivered. If the derivative exhibits activity in itself, the effective dosage can be estimated as above using the weight of the derivative, or by other means known to those skilled in the art.

Assay Examples

Inhibition of VEGF Activity

The following protocol was used to assay the compounds of the invention.

Assay Example 1

In Vitro Receptor Tyrosine Kinase Assay (VEGF Receptor KDR)

This test measures the ability of compounds to inhibit the enzymatic activity of recombinant human VEGF receptor enzymatic activity.

A 1.6-kb cDNA corresponding to the catalytic domain of VEGFR2 (KDR) (Genbank accession number AF035121 amino acid 806 to 1356) is cloned into the Pst I site of the pDEST20 Gateway vector (Invitrogen) for the production of a GST-tagged version of that enzyme. This constuct is used to generate recombinant baculovirus using the Bac-to-Bac™ system according to the manucfacturer's instructions (Invitrogen).

The GST-VEGFR2806-1356 protein is expressed in Sf9 cells (*Spodoptera frugiperda*) upon infection with recombinant baculovirus construct. Briefly, Sf9 cells grown in suspension and maintained in serum-free medium (Sf900 II supplemented with gentamycin) at a cell density of about $2 \times 10^6$ cells/ml are infected with the above-mentioned viruses at a multiplicity of infection (MOI) of 0.1 during 72 hours at 27° C. with agitation at 120 rpm on a rotary shaker. Infected cells are harvested by centrifugation at 398 g for 15 min. Cell pellets are frozen at −80° C. until purification is performed.

All steps described in cell extraction and purification are performed at 4° C. Frozen Sf9 cell pellets infected with the GST-VEGFR2806-1356 recombinant baculovirus are thawed and gently resuspended in Buffer A (PBS pH 7.3 supplemented with 1 μg/ml pepstatin, 2 μg/ml Aprotinin and leupeptin, 50 μg/ml PMSF, 50 μg/ml TLCK and 10 μM E64 and 0.5 mM DTT) using 3 ml of buffer per gram of cells. Suspension is Dounce homogenized and 1% Triton X-100 is added to the homogenate after which it is centrifuged at 22500 g, 30 min., 4° C. The supernatant (cell extract) is used as starting material for purification of GST-VEGFR2806-1356.

The supernatant is loaded onto a GST-agarose column (Sigma) equilibrated with PBS pH 7.3. Following a four column volume (CV) wash with PBS pH 7.3+1% Triton X-100 and 4 CV wash with buffer B (50 mM Tris pH 8.0, 20% glycerol and 100 mM NaCl), bound proteins are step eluted with 5 CV of buffer B supplemented with 5 mM DTT and 15 mM glutathion. GST-VEGFR2806-1356 enriched fractions from this chromatography step are pooled based on U.V. trace i.e. fractions with high O.D.280. Final GST-VEGFR2806-1356 protein preparations concentrations are about 0.7 mg/ml with purity approximating 70%. Purified GST-VEGFR2806-1356 protein stocks are aliquoted and frozen at −80° C. prior to use in enzymatic assay.

Inhibition of VEGFR/KDR is measured in a DELFIA™ assay (Perkin Elmer). The substrate poly(Glu4, Tyr) is immobilized onto black high-binding polystyrene 96-well plates. The coated plates are washed and stored at 4° C. During the assay, the enzyme is pre-incubated with inhibitor and Mg-ATP on ice in polypropylene 96-well plates for 4 minutes, and then transferred to the coated plates. The subsequent kinase reaction takes place at 30° C. for 10-30 minutes. ATP concentrations in the assay are 0.6 uM for VEGFR/KDR (2× the Km). Enzyme concentration is 5 nM. After incubation, the kinase reactions are quenched with EDTA and the plates are washed. Phosphorylated product is detected by incubation with Europium-labeled anti-phosphotyrosine MoAb. After washing the plates, bound MoAb is detected by time-resolved fluorescence in a Gemini SpectraMax reader (Molecular Devices). Compounds are evaluated over a range of concentrations, and $IC_{50}$ values (concentration of compounds giving 50% inhibition of enzymatic activity) are determined. The results are shown in Table 1. In the table, "a" indicates an $IC_{50}$ value of less than 50 nanomolar; "b" indicates an $IC_{50}$ value of 50 but <100 nanomolar; "c" indicates an $IC_{50}$ value of 100 but ≧250 nanomolar; and "d" indicates an $IC_{50}$ value of ≧250 nanomolar.

TABLE 1

| Cpd No | VEGFR $IC_{50}$ (μM) |
|---|---|
| 2 | a |
| 6 | a |
| 26 | a |
| 74 | a |
| 80 | a |
| 100 | a |
| 151 | a |
| 192 | b |
| 209 | a |
| 234 | a |
| 265 | a |

Assay Example 2

VEGF-Dependent Erk Phosphorylation

Cells and growth factor: HUVEC cells are purchased from Cambrex Bio Science Walkersville, Inc and cultured according to the vendor's instructions. The full-length coding sequence of $VEGF_{165}$ is cloned using the Gateway Cloning Technology (Invitrogen) for baculovirus expression Sf9 cells. $VEGF_{165}$ is purified from conditioned media using a NaCl gradient elution from a HiTrap heparin column (GE Healthcare Life Sciences) followed by an imidazole gradient elution from a HiTrap chelating column (GE Healthcare Life Sciences), then buffer stored in PBS supplemented with 0.1% BSA and filter sterilized Cell assays: Cells are seeded at 8000 cells/well of a 96 wells plate and grown for 48 hours. Cells are then grown overnight in serum and growth factor-free medium and exposed for 1.5 h to compounds dilutions. Following a 15 min incubation in medium, $VEGF_{165}$ (150 ng/ml) cells are lysed in ice-cold lysis buffer (50 mM HEPES, pH 7.4, 150 mM NaCl, 1.5 mM $MgCl_2$, 1% Triton X-100, 10% glycerol) containing 1 mM 4-(2 aminoethyl)benzenesulfonyl fluoride hydrochloride, 200 μM sodium orthovanadate, 1 mM sodium fluoride, 10 μg/mL leupeptin, 10 μg/mL aprotinin, 1 μg/mL pepstatin and 50 μg/mL Na-p-tosyl-L-lysine chloromethyl ketone hydrochloride and processed as Western blots to detect anti-phospho ERK1/2 (T202/Y204)(Cell Signaling Technologies).

Western blot analysis: lysates samples from single treatment wells are separated on 5-20% SDS-PAGE gels and immunobloting is performed using Immobilon polyvinylidene difluoride membranes (Amersham) according to the manufacturer's instructions. The blots are washed in Tris-buffered saline with 0.1% Tween 20 detergent (TBST) and probed for antibodies against phospho-Thr202/Tyr204-ERK (Cell signaling technologies. Chemiluminescence detection (Amersham, ECL plus) is performed according to the manufacturer's instructions using a Storm densitometer (GE Healthcare; 800 PMT, 100 nM resolution) for imaging and densitometry analysis. Values of over the range of dilution are used to prepare $IC_{50}$ curves using a 4-parameter fit model. These curves are calculated using GraFit 5.0 software.

Assay Example 3

In Vivo Choroidal Neovascularization (CNV) Model

This test measures the capacity of compounds to inhibit CNV progression. CNV is the main cause of severe vision loss in patients suffering from age-related macular degeneration (AMD).

Male Brown-Norway rats (Japan Clea Co., Ltd.) were used in these studies.

Rats were anesthetized by intraperitoneal injection of pentobarbital, and the right pupil was dilated with 0.5% tropicamide and 0.5% phenylephrine hydrochloride. The right eye received 6 laser burns between retinal vessels using a slit lamp delivery system of Green laser Photocoagulator (Nidex Inc., Japan), and microscope slide glass with Heaton™ (AMO Inc) used as a contact lens. The laser power was 100 or 200 mW for 0.1 second and spot diameter was 100 μm. At the time of laser burn, bubble production was observed, which is an indication of rupture of Bruch's membrane which is important for CNV generation.

Rats were divided into the groups based on their body weight using SAS software (SAS institute Japan, R8.1) after laser irradiation (Day 0). After animals were anesthetized, and the right pupil dilated (as above mentioned), the right eye of the animal received the compound or vehicle by an injection (10 μL/eye) at doses of 10 or 3 nmol/eye on Day 3. The compounds were dissolved or suspended in CBS, PBS, or other adequate vehicles before injection.

On Day 10, the animals were anesthetized with ether, and high molecular weight fluorescein isothiocyanate (FITC)-dextran (SIGMA, 2×10$^6$ MW) was injected via a tail vein (20 mg/rat). About 30 min after FITC-dextran injection, animals were euthanized by ether or carbon dioxide, and the eyes were removed and fixed with 10% formaline neutral buffer solution. After over 1 hour of fixation, RPE-choroid-sclera flat mounts were obtained by removing cornea, lens and retina from the eyeballs. The flat mounts were mounted in 50% glycerol on a microscope slide, and the portion burned by laser was photographed using a fluorescence microscope (Nikon Corporation, excitation filter:465-495 nm, absorption filter:515-555 nm). The CNV area was obtained by measurement of hyper-fluorescence area observed on the photograph using Scion image.

The average CNV area of 6 burns was used as an individual value of CNV area, and the average CNV area of compound treated group was compared with that of the vehicle-treated group. Results with some compounds of the present invention are shown in Table 2 and are indicated as % of inhibition of CNV progression ("A" indicates greater than or equal to 60% inhibition, and "B" indicates ≧40% to <60% inhibition).

TABLE 2

| Cpd. No. | Dose (nmol/eye) | Inhibition of CNV progression |
| --- | --- | --- |
| 2 | 10 | A |
|   | 3  | B |
| 6 | 10 | A |
|   | 3  | B |
| 26 | 10 | A |
|    | 3  | B |
| 74 | 10 | A |
|    | 3  | A |
| 192 | 3 | B |
| 234 | 3 | B |

Assay Example 4

VEGF-Induced Retinal Vascular Permeability in Rabbits

Materials and Methods

This test measured the capacity of compounds to inhibit VEGF-induced retinal vascular permeability. Vascular permeability is the cause of severe vision loss in patients suffering from age-related macular degeneration (AMD). Female Dutch rabbits (~2 kg; Kitayama LABES CO., LTD, Nagano, Japan) were anesthetized with pentobarbital and topically with 0.4% oxybuprocaine hydrochloride. Test articles or vehicle were injected into vitreous cavity after the dilation of the pupils with 0.5% tropicamide eye drop. Recombinant human VEGF$_{165}$ (500 ng; Sigma-Aldrich Co., St Louis, Mo.) was injected intravitreously 48 hr prior to the measurement of vitreous fluorescein concentration. Rabbits were anesthetized with pentobarbital and sequentially injected sodium fluorescein (2 mg/kg) via the ear vein. Pupils were dilated with 0.5% tropicamide eye drop, and ocular fluorescein levels were measured using the FM-2 Fluorotron Master (Ocumetrics, Mountain View, Calif.) 30 min after fluorescein injection. The fluorescein concentrations in vitreous were obtained at data points that are 0.25 mm apart from posterior-end along an optical axis. Vitreous fluorescence concentration was considered fluorescein leakage from retinal vasculature. The average fluorescence peaks of the test article treated groups were compared with that of the vehicle-treated group. Compound 26 and 74 showed a significant inhibition of the leakage of fluorescein compared with the vehicle-treated group.

What is claimed is:

1. A compound selected from the group consisting of

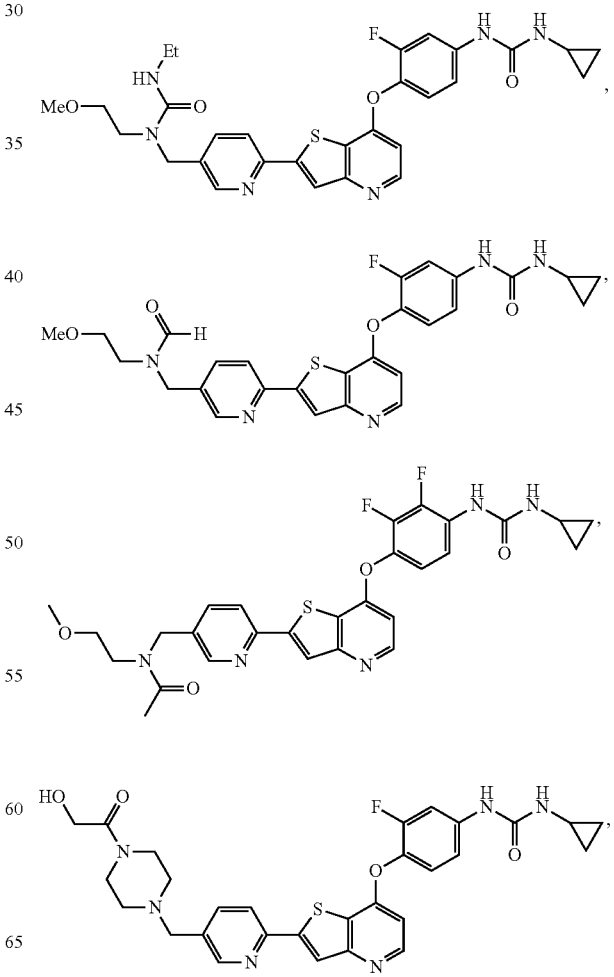

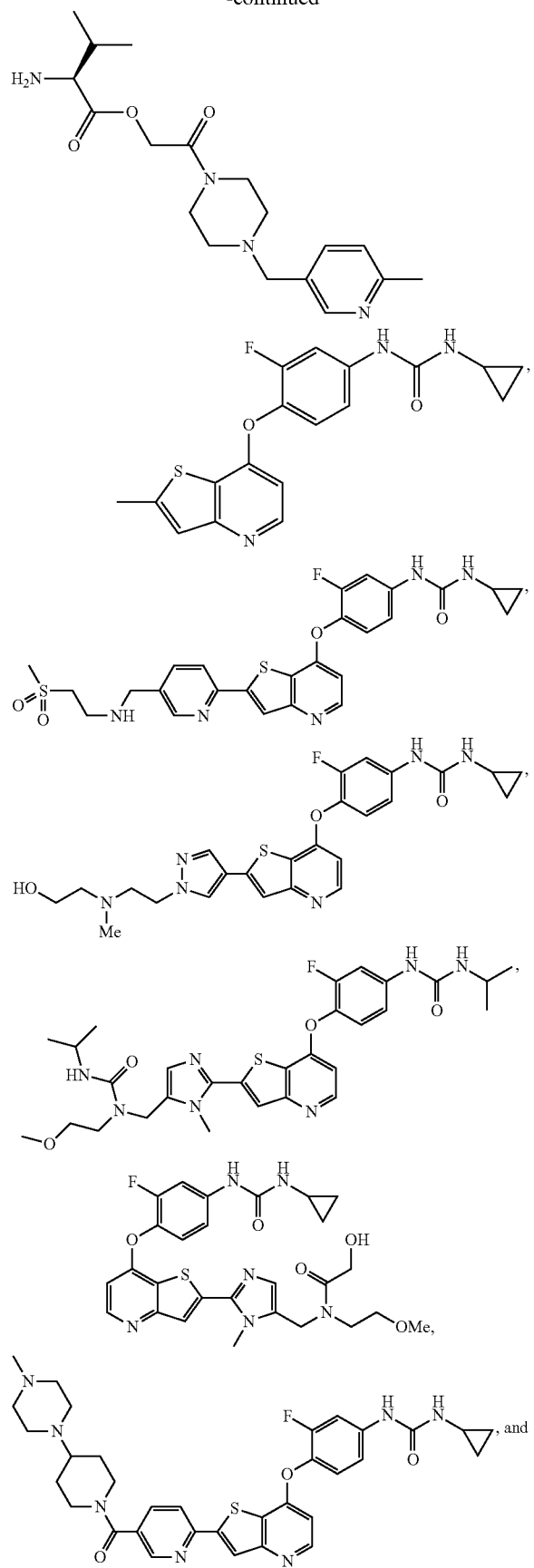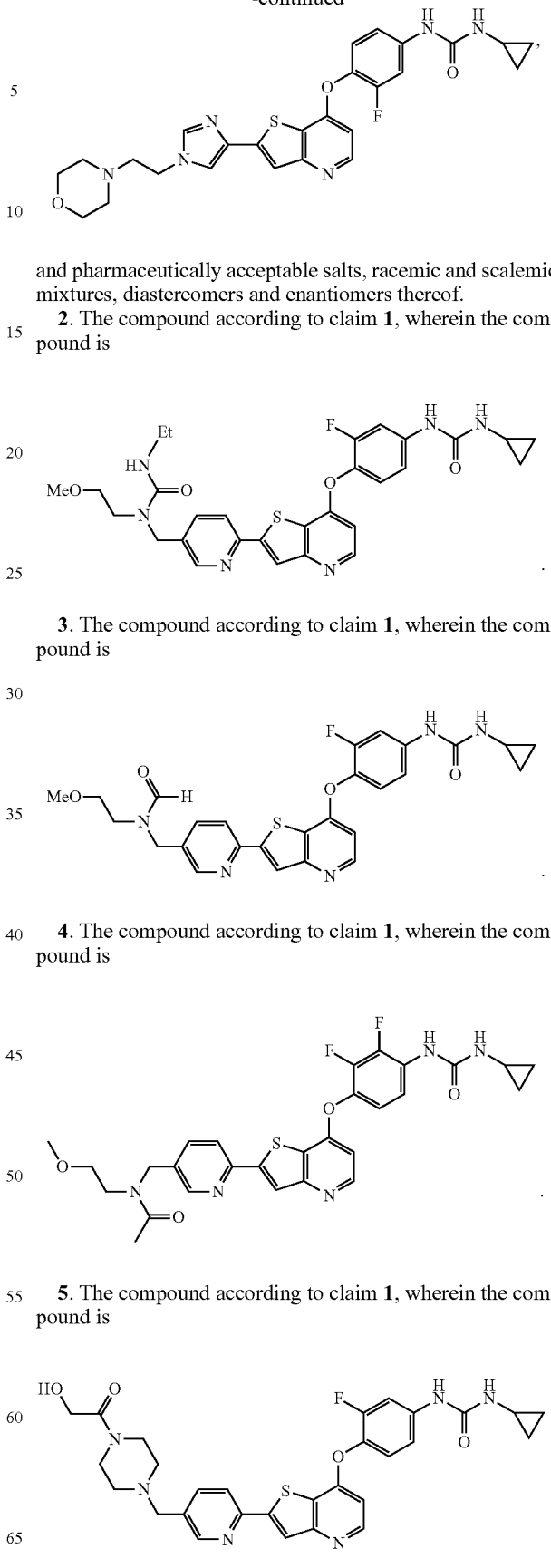
and pharmaceutically acceptable salts, racemic and scalemic mixtures, diastereomers and enantiomers thereof.
2. The compound according to claim 1, wherein the compound is
3. The compound according to claim 1, wherein the compound is
4. The compound according to claim 1, wherein the compound is
5. The compound according to claim 1, wherein the compound is 6. The compound according to claim 1, wherein the compound is
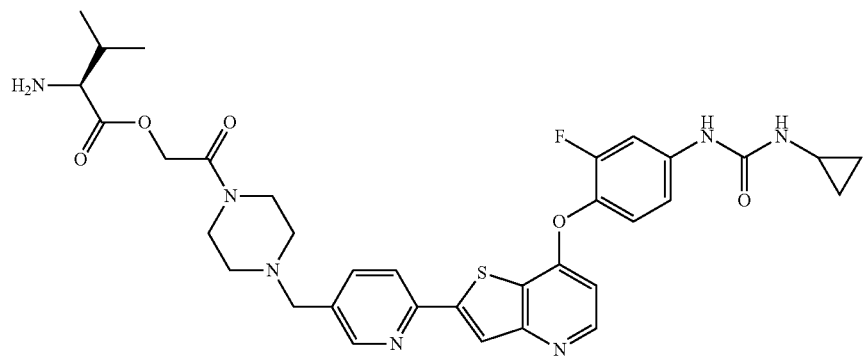
7. The compound according to claim 1, wherein the compound is
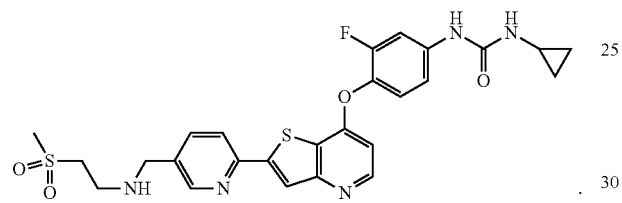
.
8. The compound according to claim 1, wherein the compound is
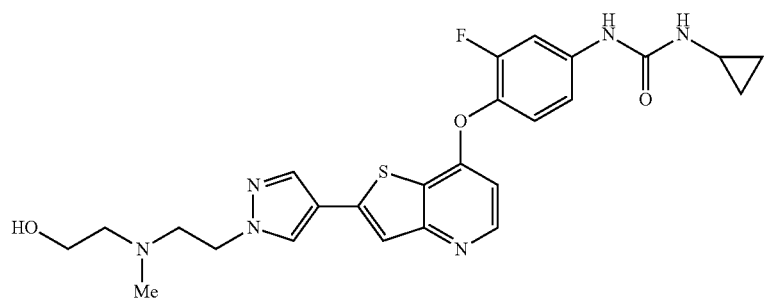
.
9. The compound according to claim 1, wherein the compound is
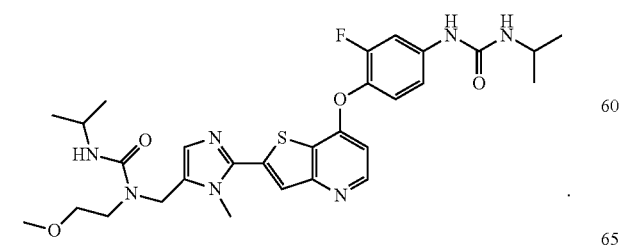

10. The compound according to claim 1, wherein the compound is

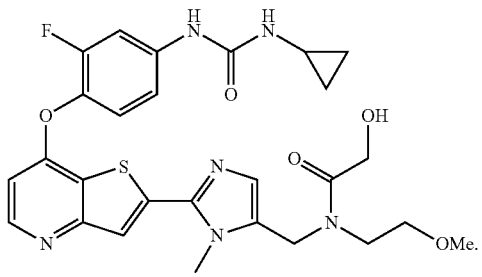 [SMILES: COCCN(Cc1cnc(-c2cc3nccc(Oc4ccc(NC(=O)NC5CC5)cc4F)c3s2)n1C)C(=O)CO]

11. The compound according to claim 1, wherein the compound is

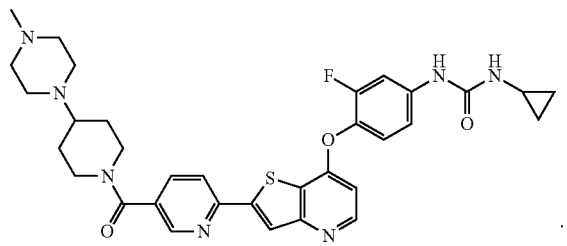 [SMILES: CN1CCN(C2CCN(C(=O)c3ccc(-c4cc5nccc(Oc6ccc(NC(=O)NC7CC7)cc6F)c5s4)nc3)CC2)CC1]

12. The compound according to claim 1, wherein the compound is

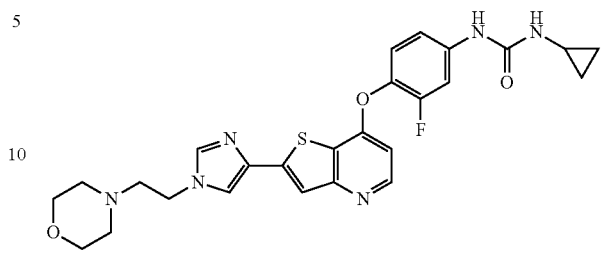

13. A composition comprising a compound according to any of claims 1 to 11 and a pharmaceutically acceptable carrier.

14. A method of inhibiting or relieving an ophthalmic disease, condition or disorder, the method comprising administering to a patient in need thereof a therapeutically effective amount of a compound according to any of claims 1 to 12 or a composition thereof, wherein the ophthalmic disease, disorder or condition is selected from the group consisting of (a) a disease, disorder or condition caused by choroidal angiogenesis, (b) diabetic retinopathy and (c) retinal edema.

15. The method according to claim 14, wherein the ophthalmic disease, disorder or condition is age-related macular degeneration.

* * * * *